(12) United States Patent
Fink

(10) Patent No.: US 10,478,088 B2
(45) Date of Patent: Nov. 19, 2019

(54) DISPOSABLE CONTAMINATION PREVENTION LINERS FOR MRI MACHINES

(71) Applicant: Michael F. Fink, Halethorpe, MD (US)

(72) Inventor: Michael F. Fink, Halethorpe, MD (US)

( * ) Notice: Subject to any disclaimer, the term of this patent is extended or adjusted under 35 U.S.C. 154(b) by 1008 days.

(21) Appl. No.: 14/939,192

(22) Filed: Nov. 12, 2015

(65) Prior Publication Data

US 2016/0135896 A1    May 19, 2016

Related U.S. Application Data

(60) Provisional application No. 62/078,535, filed on Nov. 12, 2014.

(51) Int. Cl.
| | |
|---|---|
| *A61B 6/00* | (2006.01) |
| *A61B 5/055* | (2006.01) |
| *A61B 46/10* | (2016.01) |
| *A61B 46/20* | (2016.01) |

(52) U.S. Cl.
CPC ............ *A61B 5/055* (2013.01); *A61B 5/0555* (2013.01); *A61B 46/10* (2016.02); *A61B 6/4423* (2013.01); *A61B 2046/205* (2016.02); *A61B 2562/247* (2013.01)

(58) Field of Classification Search
CPC ... A61B 6/00; A61B 6/10; A61F 1/043; A61F 2013/16
See application file for complete search history.

(56) References Cited

U.S. PATENT DOCUMENTS

| | | | |
|---|---|---|---|
| 3,761,973 A | * 10/1973 | Leventhal | ............... A61F 5/485 5/484 |
| 4,869,049 A | 9/1989 | Richards et al. | |
| 4,910,819 A | * 3/1990 | Brown | ................. A61G 7/0502 378/209 |
| 4,991,242 A | 2/1991 | Brown | |
| 5,590,512 A | 1/1997 | Richards et al. | |
| 5,590,655 A | 1/1997 | Hussman | |
| 6,006,370 A | * 12/1999 | Wu | ........................ A47K 13/16 4/244.3 |
| 6,093,255 A | 7/2000 | Smith et al. | |
| 6,170,240 B1 | 1/2001 | Jacoby et al. | |
| 6,401,265 B1 | 6/2002 | Kao et al. | |
| 6,857,778 B2 | 2/2005 | Mun et al. | |

(Continued)

FOREIGN PATENT DOCUMENTS

EP    0930853 B1    6/2004
JP    2001286460 A    10/2001

*Primary Examiner* — James S. McClellan
(74) *Attorney, Agent, or Firm* — Edell, Shapiro & Finnan, LLC

(57) ABSTRACT

A pack of disposable multi-layered liner sheets suitable for covering non-planar surfaces of medical scanners having a long, hard to clean, bore or tunnel, particularly MRI scanners, to establish a sterile patient environment. Liner sheets are connected end-to-end in a stack by an adhesive or a linear array of perforations to respective succeeding and preceding sheets of the pack. In one embodiment, the pack is secured inside the bore by pegs on the top side of the pack engaging strategically placed clips attached to the bore wall. In other embodiments, the pack is secured inside the bore by opposing sides of a backing layer extending laterally beyond the liner sheets to engage a groove in guide rails affixed inside the bore.

25 Claims, 22 Drawing Sheets

(56) References Cited

U.S. PATENT DOCUMENTS

| | | | |
|---|---|---|---|
| 7,044,132 B2 | 5/2006 | Masini | |
| 7,389,550 B2 * | 6/2008 | Park | A47K 13/16 4/244.1 |
| 7,465,089 B2 * | 12/2008 | Battle | A61B 6/00 378/204 |
| 7,757,467 B2 | 7/2010 | Chomik et al. | |
| 8,035,375 B2 | 10/2011 | Atkins et al. | |
| 8,613,546 B2 | 12/2013 | O'Connor et al. | |
| 2003/0181810 A1 | 9/2003 | Murphy et al. | |
| 2006/0079748 A1 | 4/2006 | Murphy et al. | |
| 2008/0023009 A1 | 1/2008 | Czop | |
| 2008/0216844 A1 * | 9/2008 | Olfert | A61B 6/4423 128/856 |
| 2011/0281064 A1 | 11/2011 | Murphy et al. | |
| 2012/0237000 A1 * | 9/2012 | Rahme | A61B 6/10 378/204 |
| 2013/0092177 A1 * | 4/2013 | Chua | A61B 46/10 128/855 |
| 2014/0230850 A1 | 8/2014 | Rapoport | |
| 2014/0271042 A1 | 9/2014 | Widitora et al. | |

\* cited by examiner

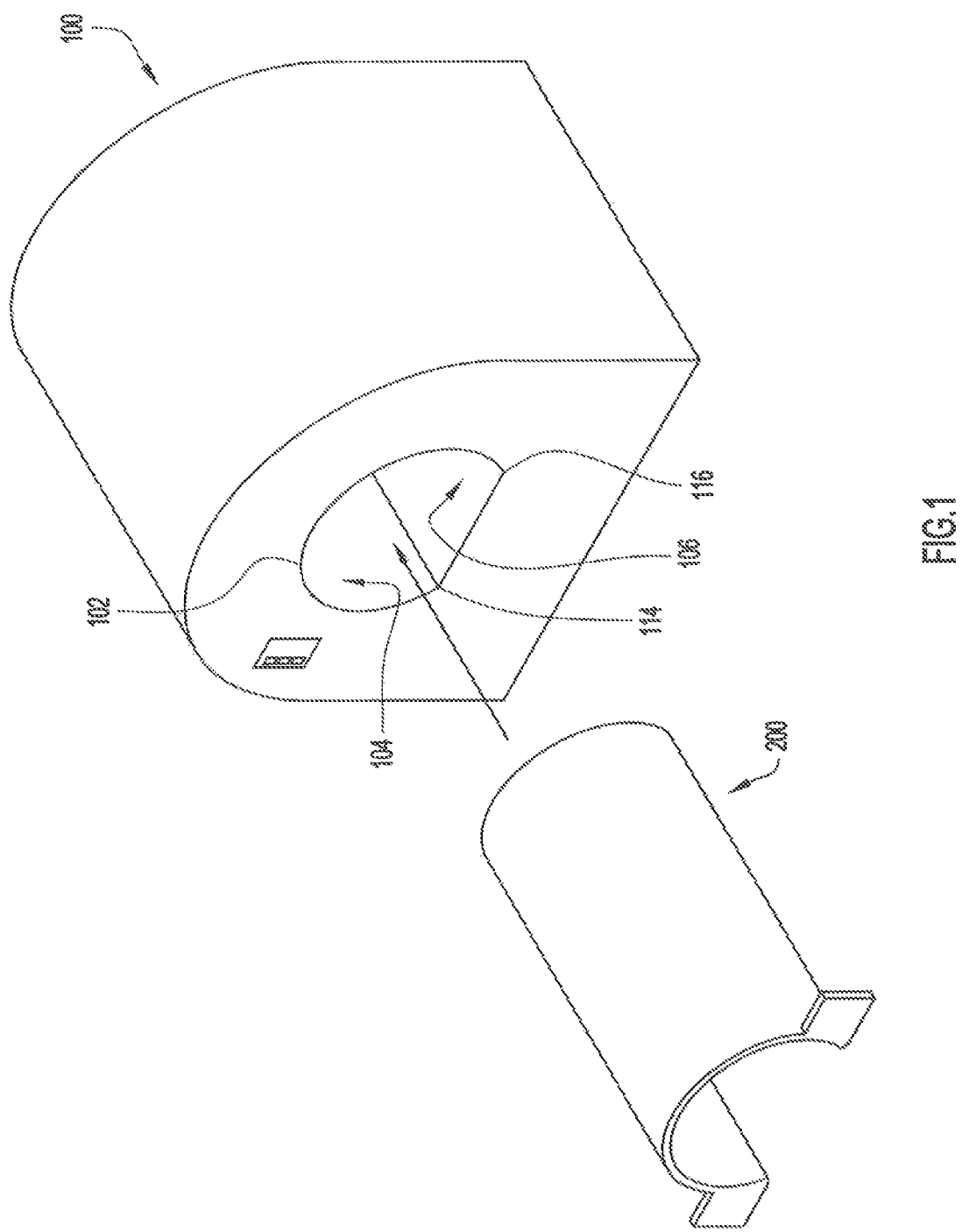

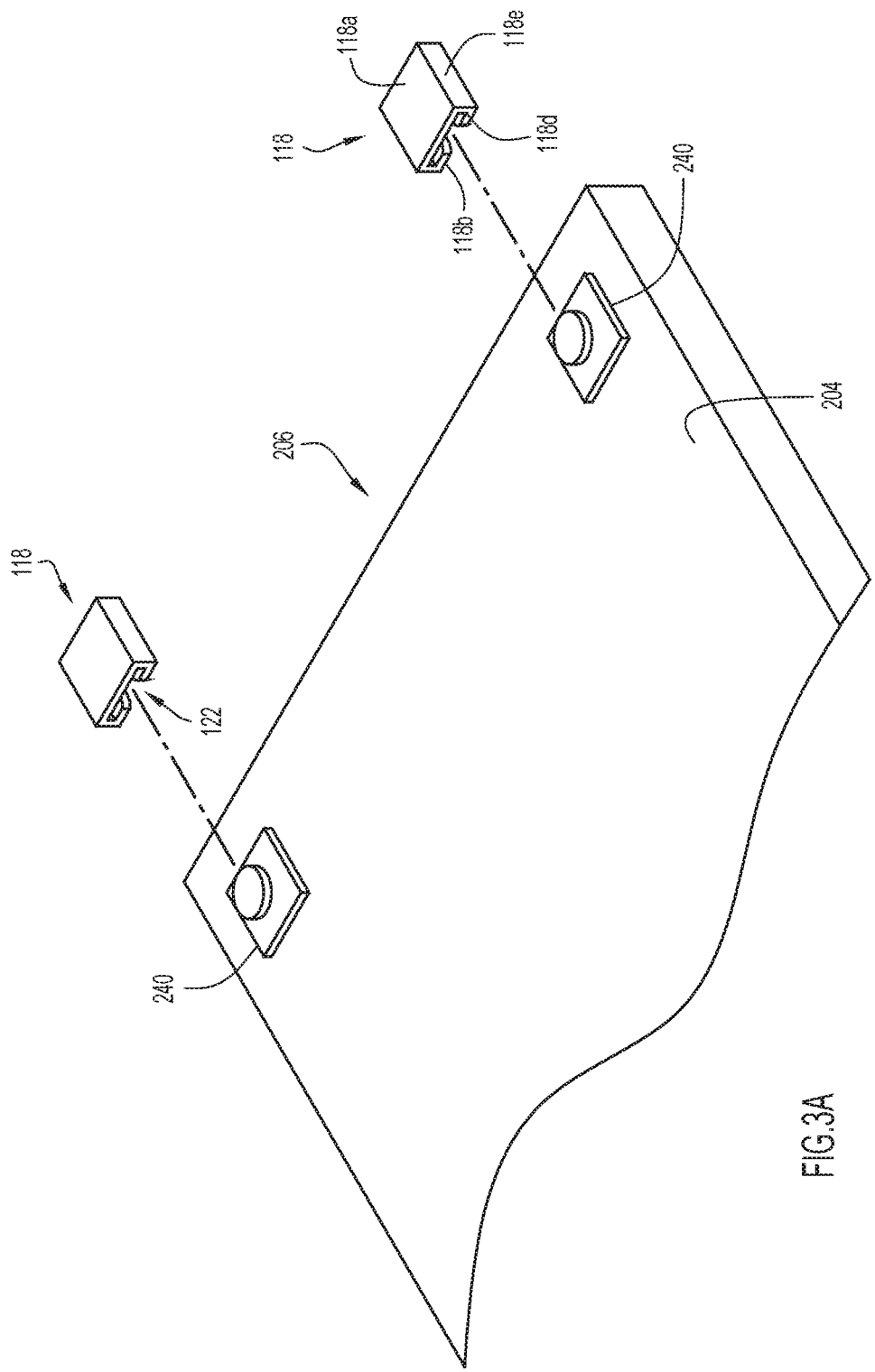

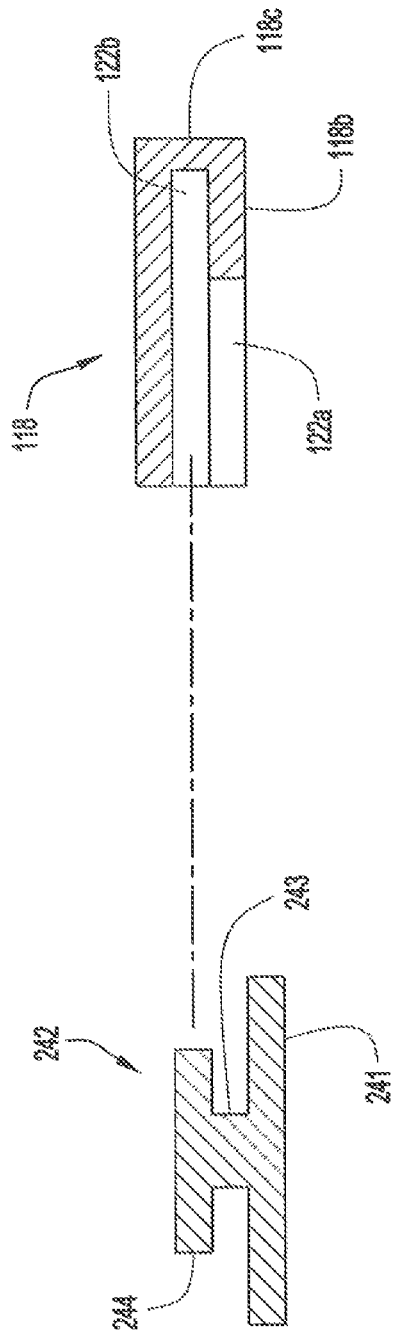

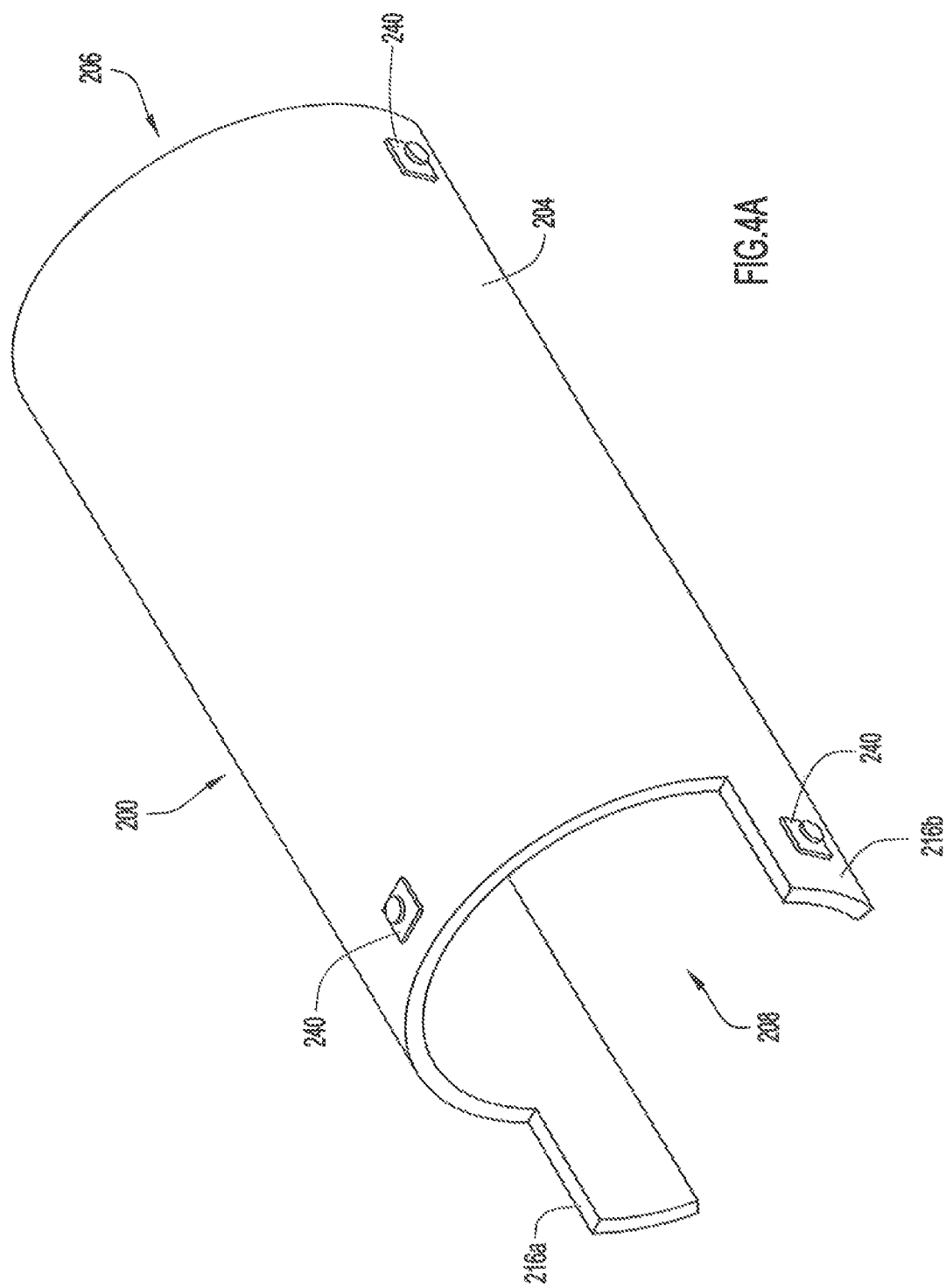

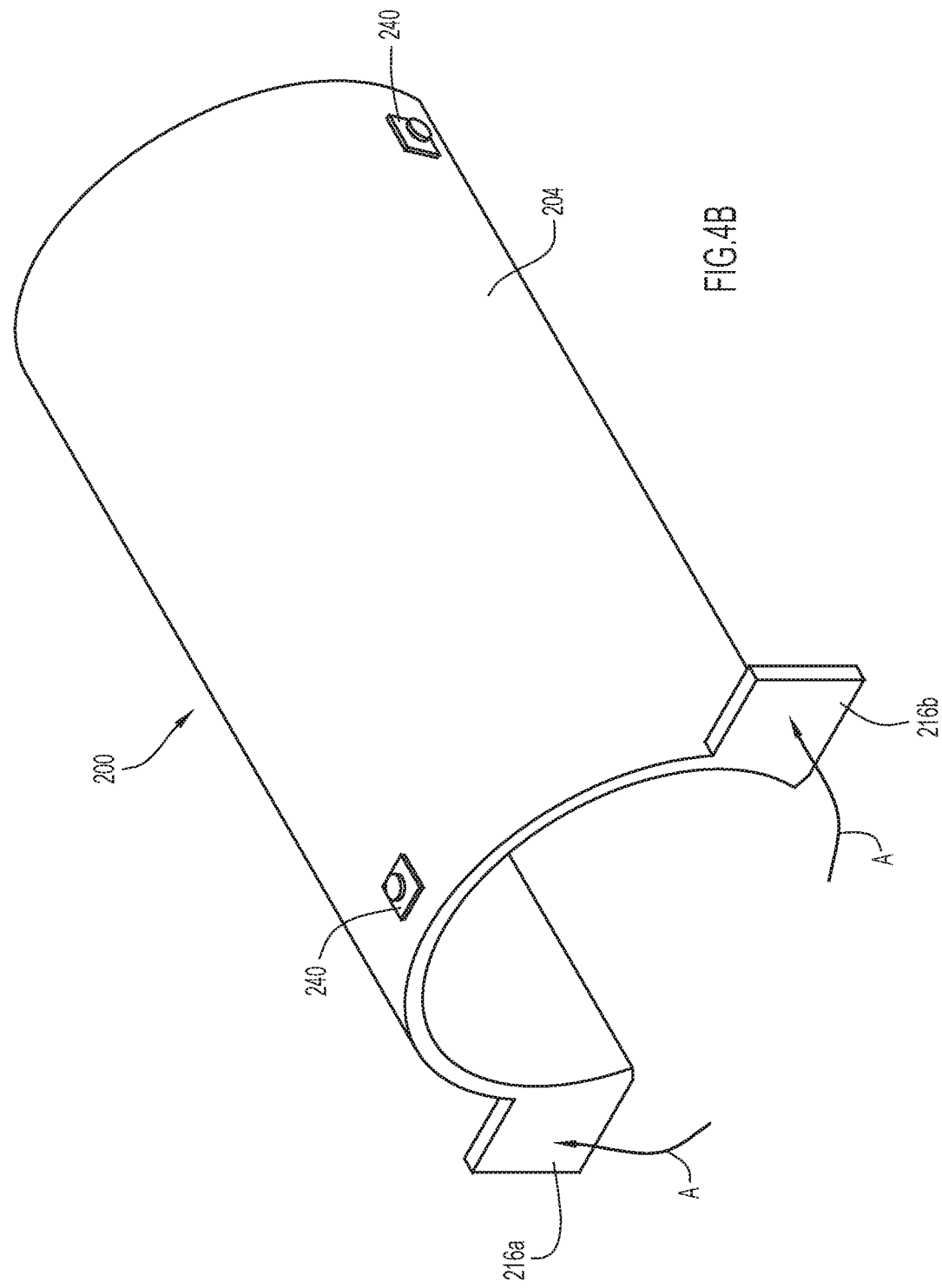

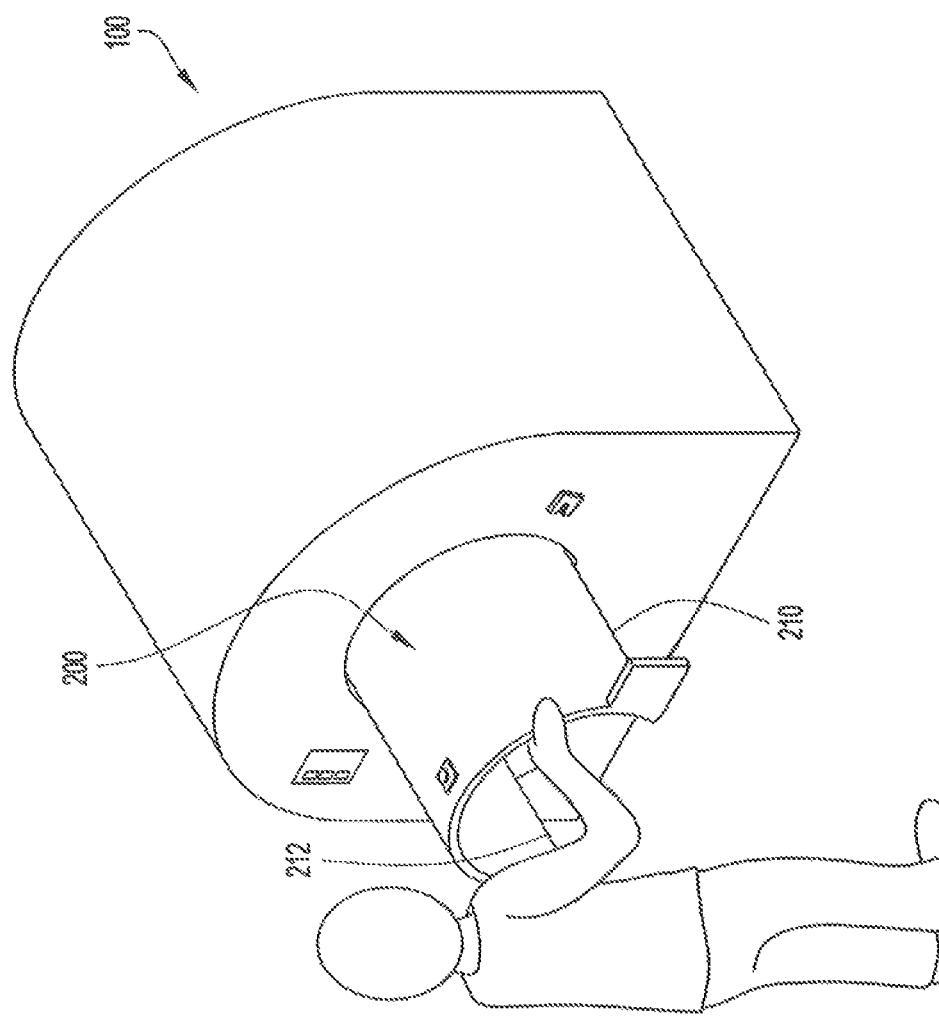

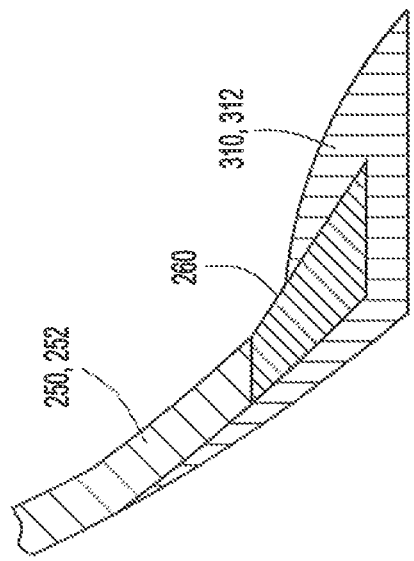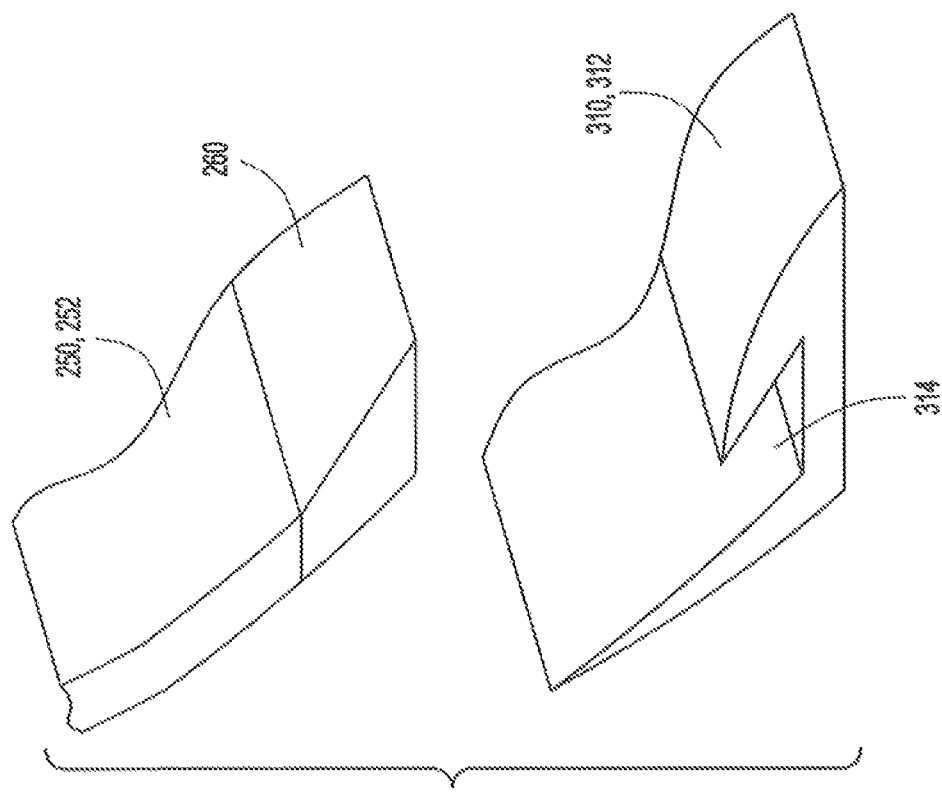

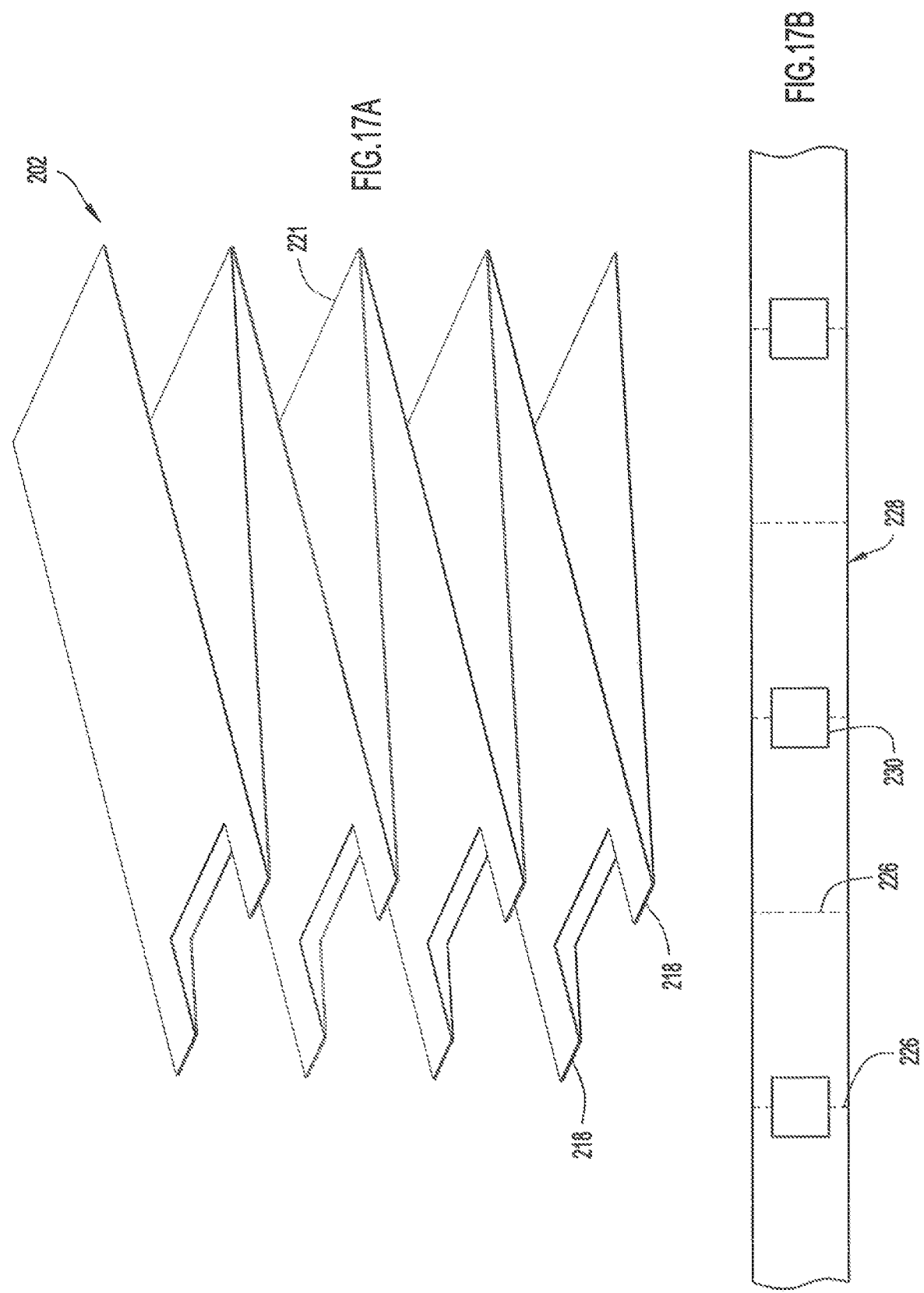

DISPOSABLE CONTAMINATION PREVENTION LINERS FOR MRI MACHINES

CROSS REFERENCE TO RELATED APPLICATIONS

The present application is a non-provisional application based on and claiming priority from U.S. Provisional Application No. 62/078,535, entitled "Disposable Contamination Prevention Liners for MRI Machines" and filed Nov. 12, 2014, the disclosure which is hereby incorporated herein by reference in its entirety.

FIELD OF THE INVENTION

The present invention pertains generally to disposable multi-layered liner sheets suitable for covering the interior bore wall of medical scanners having a long, hard to clean, bore or tunnel, particularly but not restricted to MRI scanners, and to apparatus and methods for covering the interior bore wall of medical scanners, particularly MRI scanners, with disposable multi-layered liner sheets to establish and maintain a sterile field around a patient during a procedure.

BACKGROUND OF THE INVENTION

In clinical environments, such as hospitals, medical offices, imaging centers, ambulatory surgery centers, and other medical treatment facilities, a wide range of medical equipment is used to perform diagnostic, surgical and other procedures on patients. One legitimate concern these healthcare facilities are constantly addressing is the occurrence of complications during a medical procedure on an otherwise healthy patient. For instance, there is the possibly that a healthy patient may contract an infection and/or a viral or bacterial disease from other patients. As a result, more attention is being directed to establishing and maintaining sterile fields about patients and procedure sites during medical procedures.

When a procedure involves a large piece of medical equipment, establishment and maintenance of sterile fields can become a complex problem. While many safeguards are in place in healthcare facilities to address this problem, one area that is often overlooked is the MRI scanner or machine. The environment of an MRI scanner is friendly to infectious agents because the MRI scanner includes a bore having a small diameter (e.g., in the range of 54 to 60 cm) which can become warm, thus providing an environment which promotes bacteria growth. Since patients undergoing a scan must remain within the small bore for perhaps 25 to 45 minutes while breathing and possibly even coughing or sneezing, the interior bore wall surface can become coated with bacteria and viruses. Moreover, due to the length of time a patent must remain within the bore, the interior bore wall surface is often contacted by a patient undergoing a scan and cross-contamination may occur.

In a busy healthcare facility, twenty or more patients may be scanned daily. To prevent cross-contamination from one patient to another if a patient contacts the interior bore wall surface, it is imperative that the bore wall be maintained completely sterile. This can be accomplished in a number of ways.

One way is to fully sterilize the bore wall between each use of the MRI scanner or machine. Typically, personnel of a healthcare facility will spray a decontamination liquid on the bore wall and then scrub the wall. See, for example, U.S. Pat. No. 6,093,255 (Smith et al.), the entire contents of which are incorporated herein by reference. However, cleaning can be a difficult process. Due to the length of the bore wall and the difficulty of accessing the entire bore length, portions of the wall can be, and often are, missed. If spots are missed, or if the spray and scrub procedure is ignored due to time constrains, the opportunity for disease transmission is significant. Moreover, ensuring that the interior bore wall is completely sterile is incredibly time consuming.

Another way to maintain the interior bore wall surface of an MRI scanner (machine) completely sterile is to "drape" the interior bore wall. Draping involves covering the non-linear surface to which the patient has access with a sterile covering to prevent the patient from coming in contact with the interior bore wall surface while undergoing a procedure. Prior art attempts have included either adhesively coupling flat, rectangular sheets in layers about the entire interior non-linear surface (interior bore wall) of the MRI scanner or attaching a plastic sheet in the form of a cylindrical sleeve about the interior non-linear surface (bore wall) of the MRI machine. See, for example, U.S. Patent Publication Nos. 2003/0181810 (Murphy et al.), 2006/0079748 (Murphy et al.), 2008/0216844 (Olfert et al.), and 2013/0092177 (Chua et al.). The disclosures in those published applications are incorporated herein by reference in their entireties. However, to maintain a sterile field between usages of the MRI scanner or machine in each of these systems, the contaminated sheet must be manually removed from the interior non-linear surface (interior bore wall), another sterile sheet unpacked from its sterile packaging and, thereafter, manually attached to the interior non-linear surface (bore wall) of the MRI scanner. While removing and attaching a sterile cover sheet to the bore wall surface of the MRI machine after each usage of the machine may be less time consuming than scrubbing the MRI bore wall, it remains a labor intensive and time consuming process that reduces utilization of the MRI scanner for extended periods of time.

Thus, there is a need to provide a convenient and reliable way to establish and maintain a sterile field to prevent cross-contamination from patient to patient by pathogens in a medical imaging environment as a result of physical contact with imaging equipment, particularly the interior bore wall of an MRI scanner. Further, it is highly desirable to provide a less labor intensive and time consuming process for covering the interior bore wall of an MRI scanner to which the patient has access with a sterile covering to prevent the patient from coming in contact with the interior bore wall while undergoing a procedure.

While medical applications will be used herein for illustrative purposes and simplicity of discussion, it should be clear to those of ordinary skill in the art having the benefit of this disclosure that applications for embodiments of the present invention are not so limited. Embodiments of the present nvention can be used in any application where non-planar surfaces need to be protectively covered on a relatively large piece of equipment.

SUMMARY OF THE INVENTION

Accordingly, it is an object of the present invention to provide improved disposable multi-layered liners suitable for providing a sterile environment for a medical system. Although the invention will be described with reference to MRI scanners, the invention is applicable to any medical system having a bore or tube tier patient entry and subsequent imaging or patient treatment.

It is another object of the present invention to provide sterile disposable multi-layered liners suitable for covering the interior bore wall of medical scanners having a long, hard to clean, bore or tunnel, particularly MRI scanners.

It is a further object of the present invent to provide a pack of sterile disposable multi-layered liner sheets connected end-to-end suitable for covering the interior bore walls of medical scanners having a long, hard to clean, bore or tunnel, particularly MRI scanners.

It is still a further object of the present invention to provide improved apparatus for covering the interior bore wall of medical scanners having a long, hard to clean, bore or tunnel, particularly MRI scanners, with sterile disposable multi-layered liners to establish and maintain a sterile field around a patient during a scan.

It is yet another object of the present invention to provide an improved method for covering the interior bore wall of medical scanners having a long, hard to clean, bore or tunnel, particularly MRI scanners, with sterile disposable multi-layered liners to establish and maintain a sterile field around a patient during a scan.

In its most broadest aspect, the present invention is directed to a pack of multiple "tear-away" sterile liner sheets with the sheets removably attached end-to-end. The liner sheets are removably secured to and cover the interior wall of a scanner bore to maintain a clean and sanitary environment between each patient procedure, with the exposed lowermost sheet of the pack facing a patient in the scanner bore.

In another aspect of the present invention, there is provided a pack of multiple "tear-away" sterile liner sheets having a pack backing layer of sturdy material by which all the multiple "tear-away" sterile liner sheets are supported to permit the pack to generally conform to the MRI bore wall and prevent sagging. The pack backing layer has flaps on opposite sides of its trailing end to engage the front surface of the MRI machine. The flaps include locking pegs adapted to engage respective locking receptacles on the front wall of the MRI machine. The engagement between the pack backing layer and the MRI machine serves to immobilize the pack of liner sheets and allow simple release so the pack can be easily removed once all liner sheets are used.

In a further aspect of the present invention, there is provided a pack of multiple "tear-away" sterile liner sheets having a pack backing layer of sturdy material for supporting all the multiple "tear-away" sterile liner sheets. The pack backing layer includes attachment means to permit the pack of liner sheets to be secured inside the MRI bore or tunnel in such a manner that the pack generally conforms to the MRI bore wall without sagging.

In one embodiment of the present invention, a pack of multiple "tear-away" sterile liner sheets has a pack backing layer of sturdy material which includes locking pegs on its top side (the side facing the MRI bore wall) which are adapted to cooperate with strategically placed locking receptacles or clips secured to the MRI bore wall to facilitate installation of the liner sheets inside the MRI bore.

In another embodiment of the present invention, a pack of multiple "tear-away" liner sheets has a pack backing layer of sturdy material which extends laterally outward beyond the liner sheets and cooperates with guide rails affixed inside the MRI bore to facilitate installation of the liner sheets inside the MRI bore. The guide rails generally extend the length of the MRI bore and have a groove configured to receive an edge of the outwardly extending pack backing layer.

In a further embodiment of the present invention, a pack of multiple "tear-away" liner sheets has a pack backing layer of sturdy material which extends laterally outward beyond the liner sheets and includes contour-shaped inserts attached to laterally extending portions of the backing layer. The contour-shaped inserts are adapted to cooperate with guide rails affixed inside the MRI bore to facilitate installation of the liner sheets inside the MRI bore. The guide rails generally extend the length of the MRI bore and have a contour-shaped groove configured to receive the contour-shaped inserts of the packing backing layer.

In one particular implementation of the present invention, the multiple "tear-away" sterile liner sheets are provided as a series of end-to-end connected sheets in a stack, the sheets being attached to one another at their ends using linear arrays of suitable releasable adhesive material.

In another particular implementation of the present invention, the multiple "tear-away" sterile liner sheets are provided as a series of end-to-end connected sheets in a stack, the sheets being attached to one another at their ends by linear perforations extending transversely across the sheets at their ends.

The above mentioned and other objects, features and advantages of the present invention, as well as the manner of attaining them, will become better understood upon consideration of the following definitions, descriptions and descriptive figures of specific embodiments thereof, wherein like reference characters in the various figures are utilized to designate the same or similar components. While these descriptions go into specific details of the invention, it should be understood that variations may and do exist and would be apparent to those skilled in the art based on the descriptions herein.

BRIEF DESCRIPTION OF THE DRAWINGS

FIG. 1 is a simplified exploded view in perspective diagrammatically illustrating a pack of liner sheets according to one or more embodiments of the present invention as it is being deployed in place in a bore of an exemplary MRI machine.

FIG. 3A is a detailed top view in perspective of an end portion of the pack of liner sheets of FIGS. 2A and 2B diagrammatically illustrating engagement between the pack locking pegs on the backing layer and locking receptacles provided in a bore of an MRI machine according to an embodiment of the present invention.

FIG. 3B is an enlarged cross-sectional view of the pack locking pegs and the locking receptacles of FIG. 3A diagrammatically illustrating engagement between the pack locking pegs and the locking receptacles.

FIG. 4A is a simplified view in perspective of the pack of liner sheets of FIGS. 2A and 2B contoured as it would appear prior to being deployed in place in a bore of an MRI machine.

FIG. 4B is a simplified view in perspective of the pack of liner sheets of FIGS. 2A and 2B contoured as it would appear when deployed in place in a bore of an MRI machine.

FIG. 5 is a view in perspective of the pack of liner sheets of FIGS. 2A and 2B diagrammatically illustrating the pack being deployed by an MRI operator in a bore of an exemplary MRI machine in accordance with an embodiment of the present invention.

FIG. 14A is a fragmentary perspective view illustrating a laterally extending side portion of FIG. 13 and a guide rail for securing the pack inside a bore of an MRI machine.

FIG. 14B is a cross-sectional view illustrating the laterally extending side portion of FIG. 14A secured within a groove of the guide rail of FIG. 14A as it would appear when deployed in place in a bore of an MRI machine according to an embodiment the present invention.

FIG. 17A is an exploded view in perspective of a pack liner sheets illustrating the sheets as a series of end-to-end connected sheets folded onto one another in a stack in accordance with an alternative embodiment of the present invention.

FIG. 17B is a top plan view of the liner sheets of FIG. 17A illustrating the sheets as they would appear prior to being folded end-to-end onto one another in a stack.

Skilled artisans ill appreciate that elements in the figures are illustrated for simplicity and clarity and have not necessarily bee been drawn to scale. For example, the dimensions of some of the elements in the figures may be exaggerated relative to other elements while elements in other figures may be omitted to help to improve understanding of embodiments of the present invention.

DETAILED DESCRIPTION OF THE INVENTION

In accordance with the principles of the invention, FIG. 1 illustrates an exemplary large piece of medical equipment 100, such as a magnetic resonance imaging (MRI) scanner or machine, which includes a bore or tunnel 102 through which a patient (not shown) is received in order to perform diagnostic, surgical, or other procedures, and a simplified pack of disposable multi-layered liner sheets 200 contoured as it would appear prior to being deployed in place in the bore of the exemplary MRI machine according to one or more embodiments of the present invention. The pack of disposable multi-layered liner sheets 200 are described in greater detail below.

Figure 6:
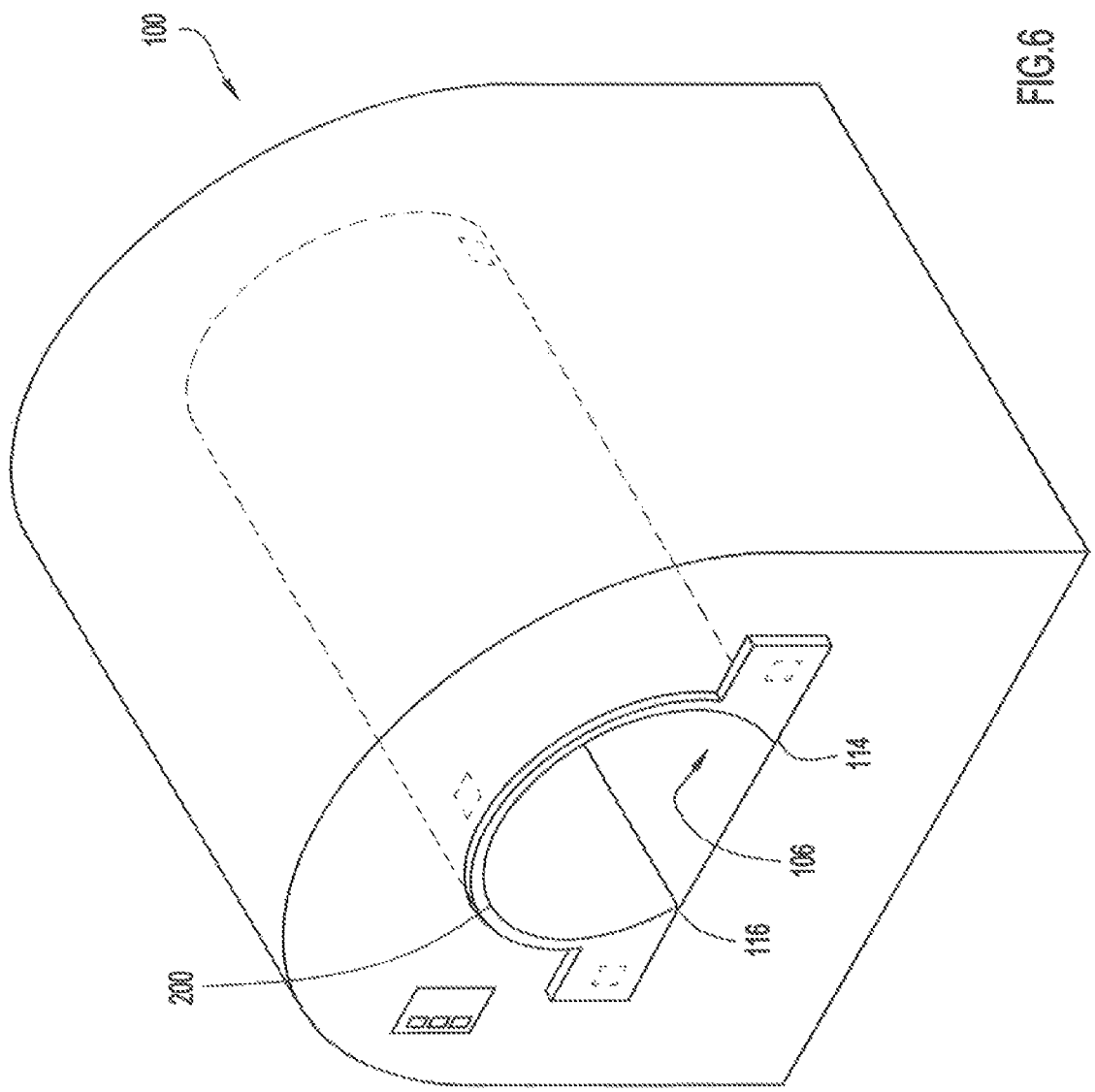
FIG. 6 is a simplified view in perspective of the pack of liner sheets of FIGS. 2A and 2B deployed in place in a bore of an exemplary MRI machine in accordance with an embodiment of the present invention.
Figure 7:
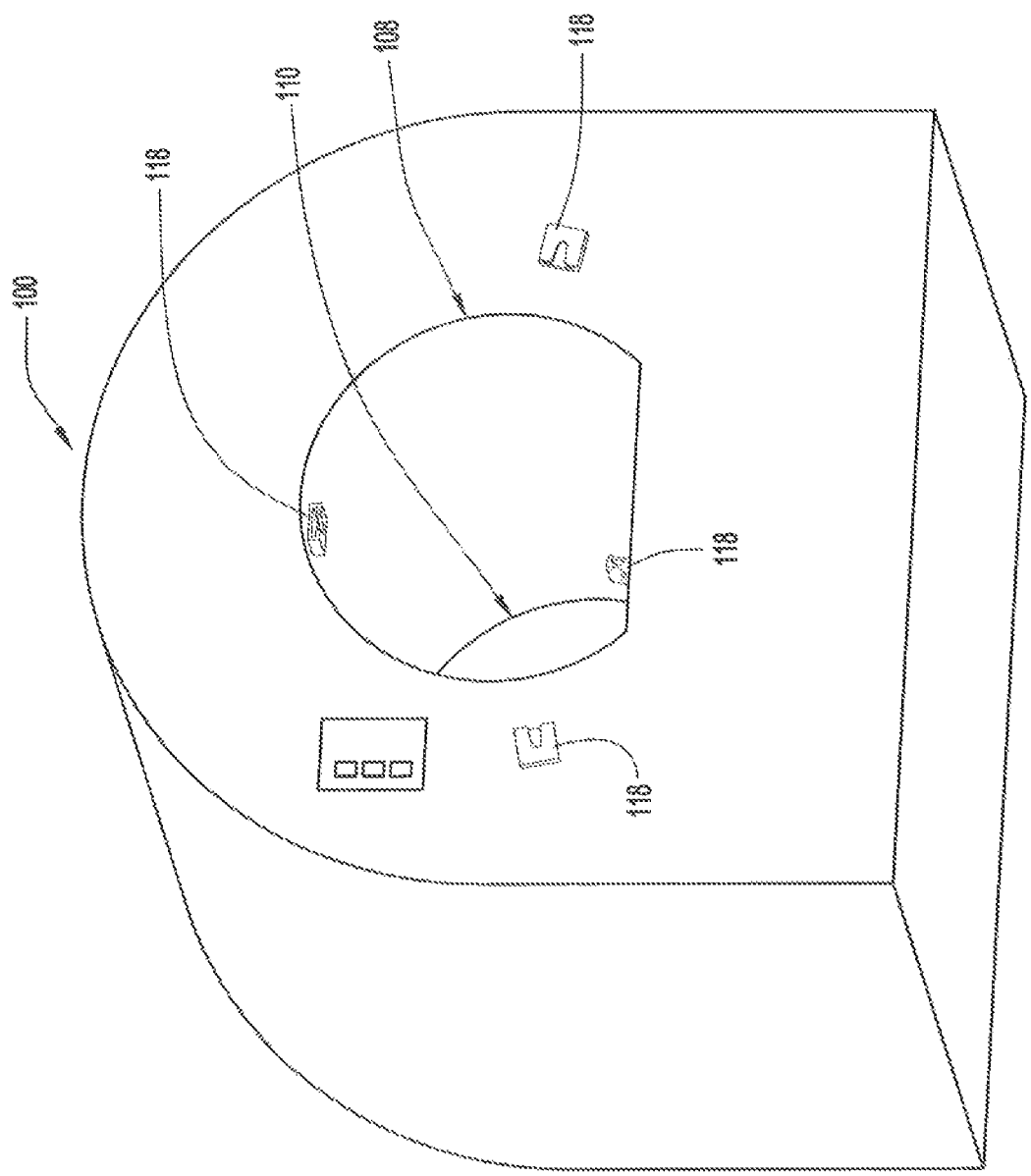
FIG. 7 is a view in perspective showing locking receptacles secured to a front surface and an interior bore wall of an exemplary MRI machine according to an embodiment of the present invention.

The bore or tunnel 102 of the exemplary MRI machine 100 of FIG. 1 has a partial non-linear bore wall surface (arcuate or curved surface) 104, a planar horizontal bore wall surface 106 that is used to advance a carriage (not shown) carrying a patient into the bore 102, and an open front end 108 and an open rear end 110 (FIG. 7). The non-linear surface 104 and the planar horizontal surface 106 extend from the open front end 108 to the open rear end 110 (FIG. 7). The bore 102 has a constant radius from one side 114 of the planar horizontal surface 106 to the other side 116 of the surface. The pack of liner sheets 200 is sufficiently soft and pliable to conform to and cover substantially the entire exposed arcuate bore wall surface 104 of the exemplary MRI scanner when placed inside the bore (FIG. 6). Additionally, the pack of liner sheets is designed to fit flush and entirely within the dimensions of the MRI bore while taking into account the variations between different manufacturer designs and specifications. While the explanatory piece of exemplary medical equipment 100 is described as an MRI machine, applications for embodiments of the present invention are not limited either to MRI machines or medical machines, as previously mentioned.

Figure 2A:
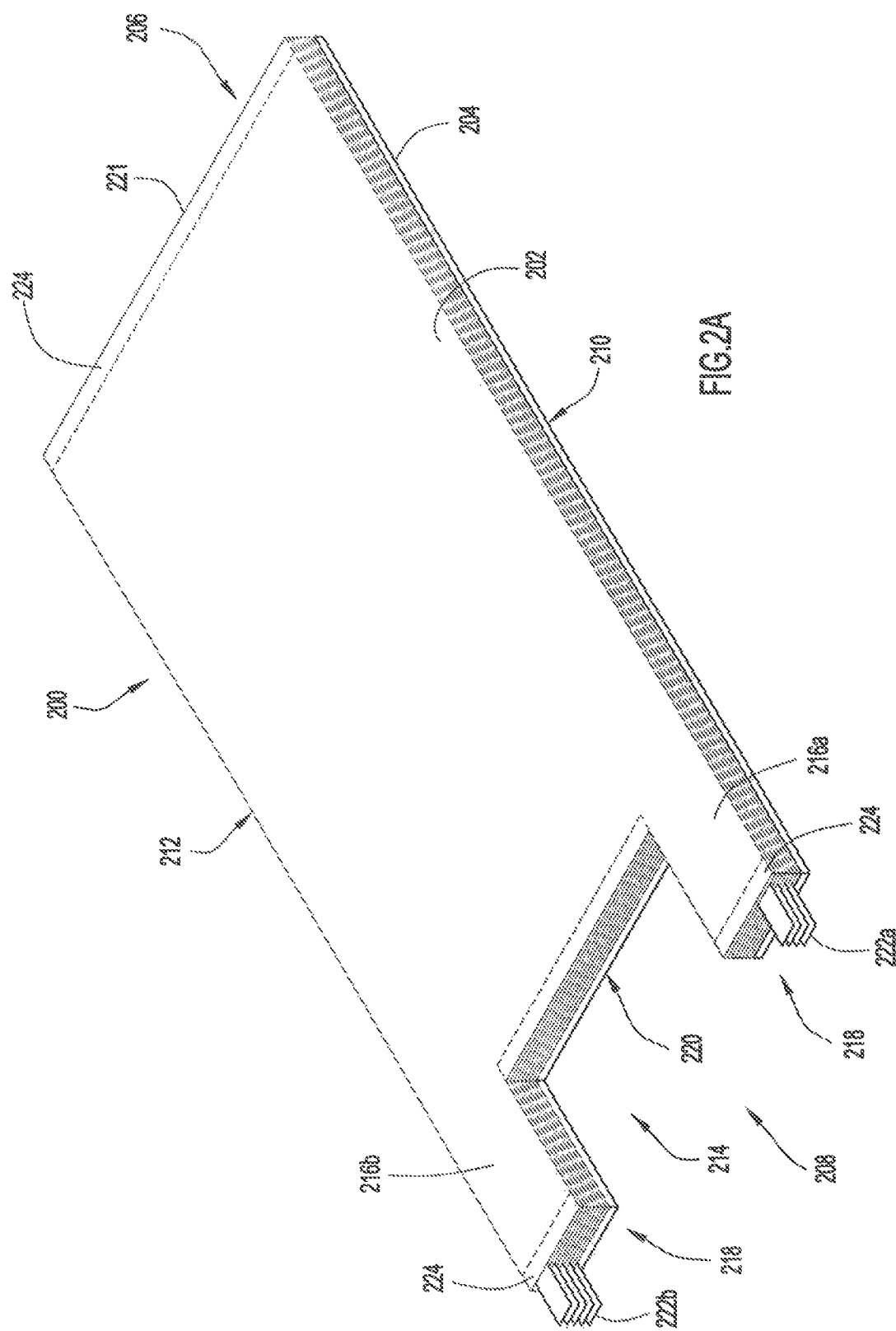
FIG. 2A is a bottom view in perspective of a pack of dispensable liner sheets for use individually in a bore of an MRI machine according to an embodiment of the present invention.

Referring to FIG. 2A, there is shown a bottom perspective view of the pack of disposable multi-layered liner sheets 200 in an assembled state. The pack 200 includes a backing layer 204 and a series of end-to-end connected liner sheets 202 in a stack. The stack of liner sheets 202 is secured to and supported by the backing layer 204 by any suitable releasable connection. The pack 200 has a generally quadrilateral shape with a leading end, generally referenced 206, a trailing end, generally referenced 208, and opposing sides 210, 212 transversely aligned to the leading end 206 and trailing end 208 (see FIGS. 2D, 2E). A notch-shaped indentation, generally referenced 214, is formed at the trailing end 208 by cutting away a center segment of the trailing end 208, i.e., cutting away a center segment at the trailing end of each liner sheet 202 and the backing layer 204. The remaining segments on opposite sides of the indentation 214 define a pair of opposing flaps 216a, 216b which engage the front face of an MRI machine (e.g., the exemplary MRI scanner 100 shown in FIG. 6) when the pack 200 is deployed inside the MRI bore. The notch-shaped indentation 214 extends inward from an outer edge 218 of the trailing end 208 and terminates at an inner edge 220.

A series of pull tabs 222a may extend outwardly from flaps 216a and a series of pull tabs 222b may extend outwardly from flaps 216b so that a used liner sheet 202 may be grasped by an operator and easily removed from the pack 200. As illustrated in FIG. 2A, the pull tabs 222a extend outward from every other flap 216a, and the pull tabs 222b extend outward from every other flap 216b in an alternating sequence. For example, if ten liner sheets (numbered 1, 2, 3 ... 10) are secured to and supported by backing layer 204, pull tabs 222a may extend outward from flaps 216a of liner sheets 1, 3, 5, 7, and 9, while pull tabs 222b may extend outward from flaps 216b of liner sheets 2, 4, 6, 8, and 10. The sequencing of the pull tabs in this manner provides extra space between pull tabs so that the pull tab of a used liner sheet 202 may be more easily grasped by an MRI operator to initiate removal of the used liner sheet from the bore of an MRI machine. While pull tabs 222a and 222b may provide a convenient means for permitting quick removal of used liner sheets 202 from an MRI bore, it will be appreciated that the pull tabs are optional and, in alternative arrangements, used liner sheets 202 may be "torn-away" from the pack of liner sheets and removed from an MRI bore by grasping other means, such as flaps 216a, 216b.

Turning again to FIG. 2A, each liner sheet of the stack of end-to-end connected liner sheets 202 may be removably attached at its leading end 206 and its trailing end 208 to a leading and trailing end of respective succeeding and preceding liner sheets 202. While any suitable releasable connection means may be used to attach the liner sheet ends to one another, such as a hook and loop connection (e.g., Velcro®), a releasable adhesive connection is preferred. For example, a patch or linear strip of "low-tack" pressure sensitive adhesive 224, such as the "low-tack" pressure sensitive adhesive used to temporarily adhere Post-It® notes to another document or other surfaces, may be positioned on a portion of the upper or lower surface of liner sheets 202 such that it engages a portion of the upper or lower surface of succeeding and preceding liner sheets 202 of the stack.

In the FIG. 2A embodiment of the present invention, the broken line configuration at the leading end 206 represents a patch or linear strip of "low-tack" pressure sensitive adhesive 224 extending transversely across a portion of the surface of liner sheets 202 adjacent edge 221 of the leading end, while the broken line configurations at the trailing end 208 represent a patch or linear strip of "low tack" pressure sensitive adhesive 224 extending transversely across a portion of the surface of the liner sheets adjacent outer edges 218 (i.e., outer edge of flaps 216a, 216b) and inner edge 220 of the trailing end. However, in an alternative implementation of the present invention, the broken line configuration extending transversely across the liner sheet 202 from pack side 210 to pack side 212 at the leading end 206 may represent a line of perforations. As shown in FIG. 2A, the line of perforations is set back from leading end edge 221 in a manner similar to the design of a legal pad. Therefore, each liner sheet 202 may be connected to the next sheet at its leading end 206 by pressure sensitive adhesive or a transversely extending line of perforations, while each liner sheet 202 may be connected to the next liner sheet at its trailing end 208 by pressure sensitive adhesive. Each of the above described connections releases individual liner sheets from the pack cleanly upon application by an MRI operator of a nominal pulling force applied along the sheet length dimension from the open front end 108 of the exemplary MRI scanner 100 shown in FIG. 1, thereby removing a used (and perhaps contaminated) liner sheet and exposing a fresh, clean, and sterile liner sheet underneath the used liner sheet (see FIG. 8).

However, in lieu of, or in addition to, the aforementioned adhesive connection locations, "low-tack" pressure sensitive adhesive 224 may be positioned at other suitable locations on the upper and/or lower surface of liner sheets 202. At the trailing end, for example, additional patches or strips of "low-tack" pressure sensitive adhesive 224 may be positioned across the entire upper and/or lower surface of flaps 216a, 216b and/or the strip of "low-tack" pressure sensitive adhesive 224 extending transversely across a portion of the surface of the liner sheets 202 adjacent inner edge 220 may be omitted. Moreover, the configuration of the pressure sensitive adhesive 224 is not limited to a patch or linear strip, but may be any other suitable configuration.

Referring again to FIG. 2A, the pull tab associated with each liner sheet 202 enables the MRI operator to easily grasp a used liner sheet, tear it away from the underlying liner sheet, and quickly remove it from within a bore of an MRI machine through the bore open front end (e.g., open front end 108 of bore 102 of the exemplary MRI machine 100 shown in FIG. 1), thus exposing the next clean, sterile liner sheet for the following patient. Thus, the "tearing-away" of the topmost liner sheet 202 in this manner from the pack of liner sheets 200 not only permits dispensing of successive sterile liner sheets from the pack of liner sheets 200 in a quick and easy manner, but permits a sterile field to be established and maintained prior to and during a patient scan in a less labor intensive and time consuming way. Further, each used (and perhaps contaminated) liner sheet may be subsequently easily disposed of in a suitably provided container (not shown).

Referring to FIGS. 17A and 17B, there is shown an alternative arrangement for attaching the stack of end-to-end connected liner sheets 202 to respective succeeding and preceding liner sheets in the pack 200. In this embodiment, liner sheets 202 are provided in the pack 200 as a series of end-to-end connected sheets folded onto one another in a stack. Each sheet is removably attached at its leading edge 221 and its trailing edge 218 to a leading edge and a trailing edge of respective succeeding and preceding sheets in the pack 200 by linear perforations 226 extending transversely across the sheets (see FIG. 17B).

As shown in FIG. 17B, an elongated substrate 228 may have a series of linear perforations 226 extending transversely across its width at spaced apart locations along the length of the substrate. The perforations 226 may be punched into elongated substrate 228 using techniques well know to one skilled in the art. In addition, a series of openings or apertures 230 may be cut or punched into a center portion of substrate 228 at locations which overlap with every other transversely extending linear perforation 226 using techniques which are also well know to one skilled in the art. The width of apertures 230 is designed to be less than the width of the substrate 228 in order to create the previously mentioned pair of flaps 216a, 216b, while the portions of the substrate 228 extending between each of linear perforations 226 define the previously mentioned series of end-to-end connected liner sheets 202. The stack of end-to-end connected liner sheets 202 shown in FIG. 17A is assembled by bending over or doubling up the substrate 228 about linear perforations 226 (posterior seam) so one liner sheet lies on another liner sheet 202 in a stacked configuration.

However, a hybrid arrangement for attaching the stack of end-to-end connected liner sheets 202 to respective succeeding and preceding liner sheets in the pack 200 may be used in the embodiments illustrated in FIGS. 2A, 2B and FIGS. 17A, 17B. In this particular implementation of the present invention, the leading end 206 of each sheet 202 is removably attached at its leading end edge 221 to a leading end edge of respective succeeding and preceding sheets in the pack 200 by linear perforations 226 extending transversely across the sheets solely at the posterior seam (i.e., the line where the posterior edges of two sheets 202 touch each other), while the trailing end 208 of each sheet 202 is removably attached at its trailing end edge 218 to a trailing end edge of respective succeeding and preceding sheets in the pack 200 by "low-tack" pressure sensitive adhesive positioned adjacent the edge. With this arrangement, each liner sheet 202 at leading end 206 is connected to the next sheet at its leading end by a perforated connection that releases each liner sheet cleanly upon application by an MRI operator of a nominal pulling force applied along the sheet length dimension from the open front end of the MRI scanner, thereby removing a used (and perhaps contaminated) liner sheet and exposing a fresh, clean, and sterile liner sheet underneath the used liner sheet (see FIG. 8).

The liner sheets 202 shown in FIGS. 2A, 2B and FIGS. 17A, 17B, as well as the liner sheets described in the hybrid arrangement, may be a substrate formed from a thin, flexible material, typically a liquid absorbent paper or composite material. For example, each liner sheet 202 may preferably be a 2-ply sheet formed from a layer of liquid absorbing material 202a backed with a layer of liquid impervious material 202b (FIG. 2C), or a 3-ply laminated sheet constructed with a layer of impervious material 202b sandwiched between two layers of liquid absorbing material 202a. While the 3-ply laminated liner sheet may work best with the liner sheets configured as shown in FIGS. 17A, 17B, the key factor is that no liquid should seep through a liner sheet 202 and contaminate the subsequent layer of liquid absorbing material 202a of the next liner sheet 202 in the pack 200. In other words, there should be no cross-contamination. In this regard, depending on the bore diameter and its configuration, the liner sheet can be designed to cover from approximately 180°-270° of the bore wall surface.

The liquid absorbing layer 202a and the liquid imperious layer 202b may be bonded together by stitching, by an adhesive or by utilizing other techniques well know to one skilled in the art. To help establish and/or maintain a sterile and sanitary MRI environment, a measured quantity of a sanitizing-disinfectant substance may be applied between the two layers of material before their joining. Alternatively, a germicide, anti-bacterial or some other protective substance may be embedded within or coated on one or both of the layers 202a, 202b.

The liquid absorbing material layer 202a may be, for example, tissue-type paper similar to the paper used on a physician's or a medical facility's examination table, while the liquid impervious material layer 201b may be a polymeric MRI transparent material, such as a polymer film (e.g., polyethylene), since these materials do not affect the transmission of magnetic radiation. Alternatively, the liner sheets may be made from waterproof Nylon, e.g., "ripstop" Nylon, backed with adhesive to be secured to a subsequent liner sheet (not shown). However, any other suitable material that does not interfere with the transmission of magnetic radiation (MRI transparent material) may be used to provide a clean and sanitary MRI environment.

In use, the layer of liquid absorbing material 202a faces inwardly towards a patient's body to prevent a patient from inadvertently contacting an MRI bore wall (e.g., bore wall 104 of exemplary MRI machine 100 shown in FIG. 1), while the layer of liquid imperious material 202b faces outwardly towards an MRI bore wall (e.g., bore wall 104 of exemplary MRI machine shown in FIG. 1) and prevents liquids from seeping through the liner sheet 202 and contaminating the subsequent layer of liquid absorbing material 202a of the next liner sheet 202 in the pack 200.

Figure 2B:
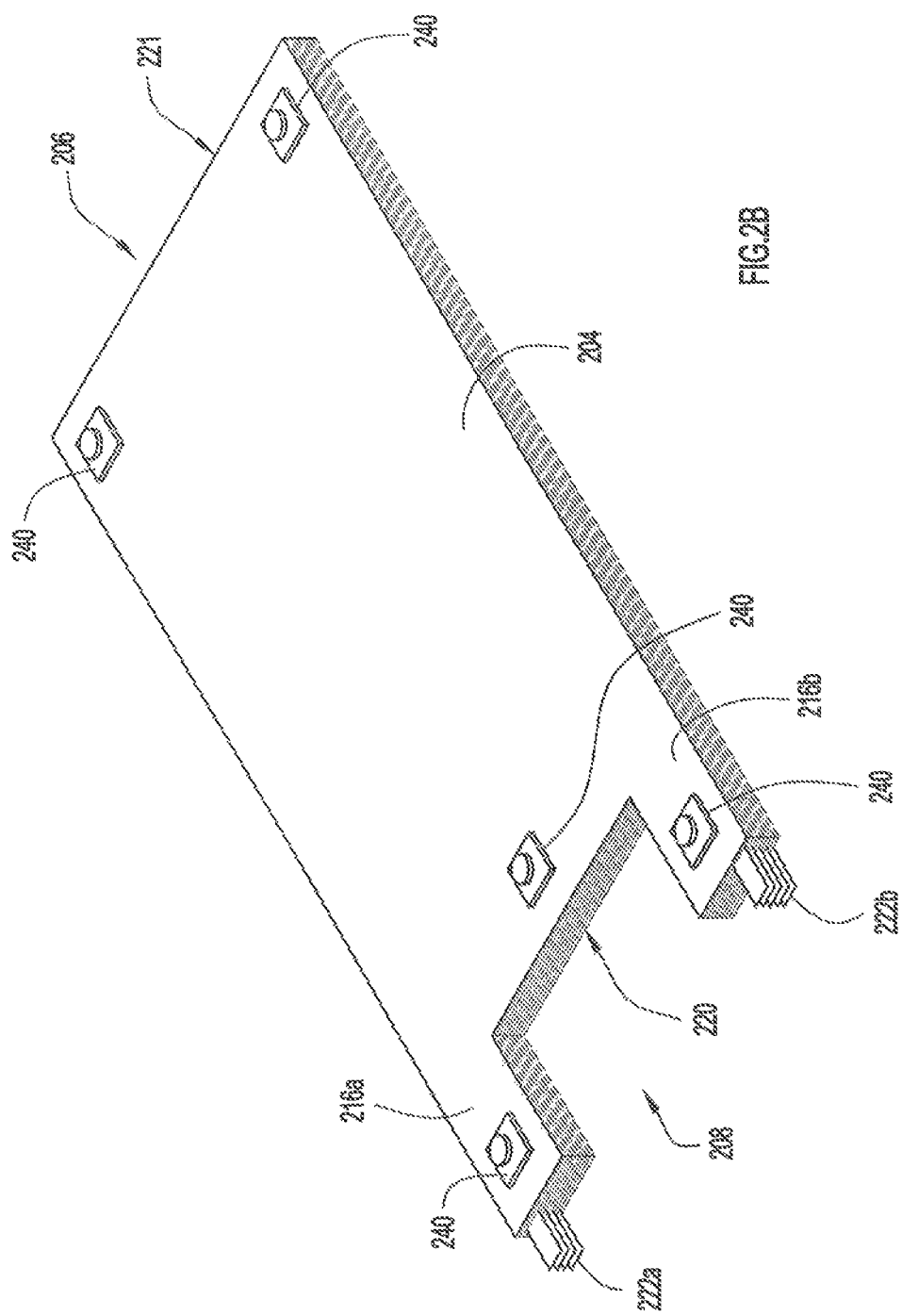
FIG. 2B is a top view in perspective of the pack of liner sheets of FIG. 2A showing a backing layer on the pack top side with locking pegs adapted to fit into and be retained by locking receptacles secured on an MRI machine according to an embodiment of the present invention.
Figure 2C:
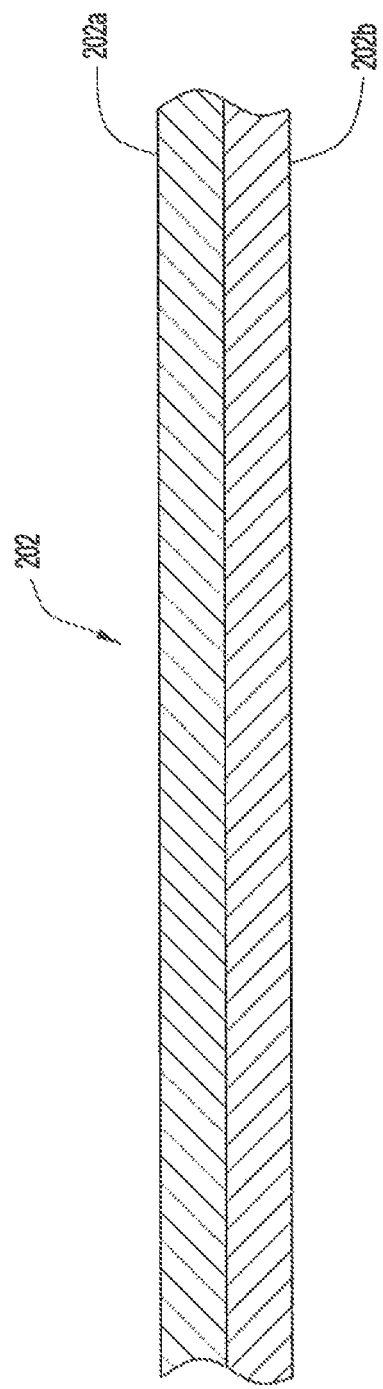
FIG. 2C is a cross-sectional view of a liner sheet from the pack of liner sheets of FIGS. 2A and 2B according to an embodiment of the present invention.
Figure 2E:
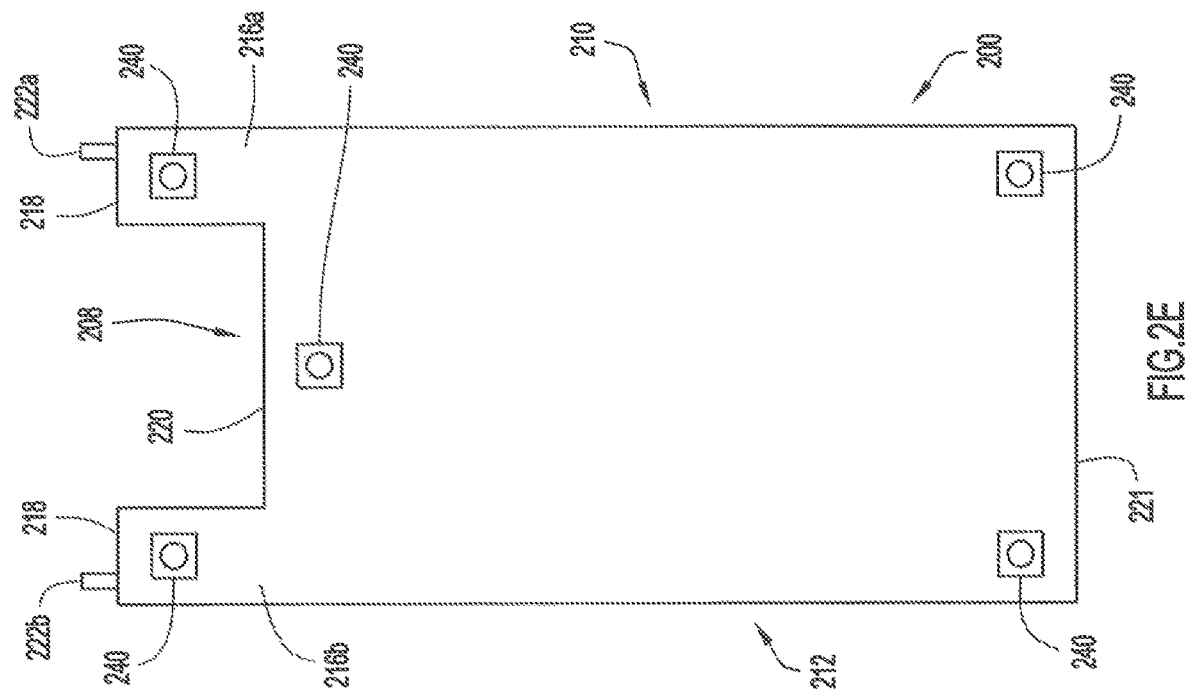
FIG. 2E is a top view in plan of the pack of liner sheets of FIGS. 2A and 2B.
Figure 2D:
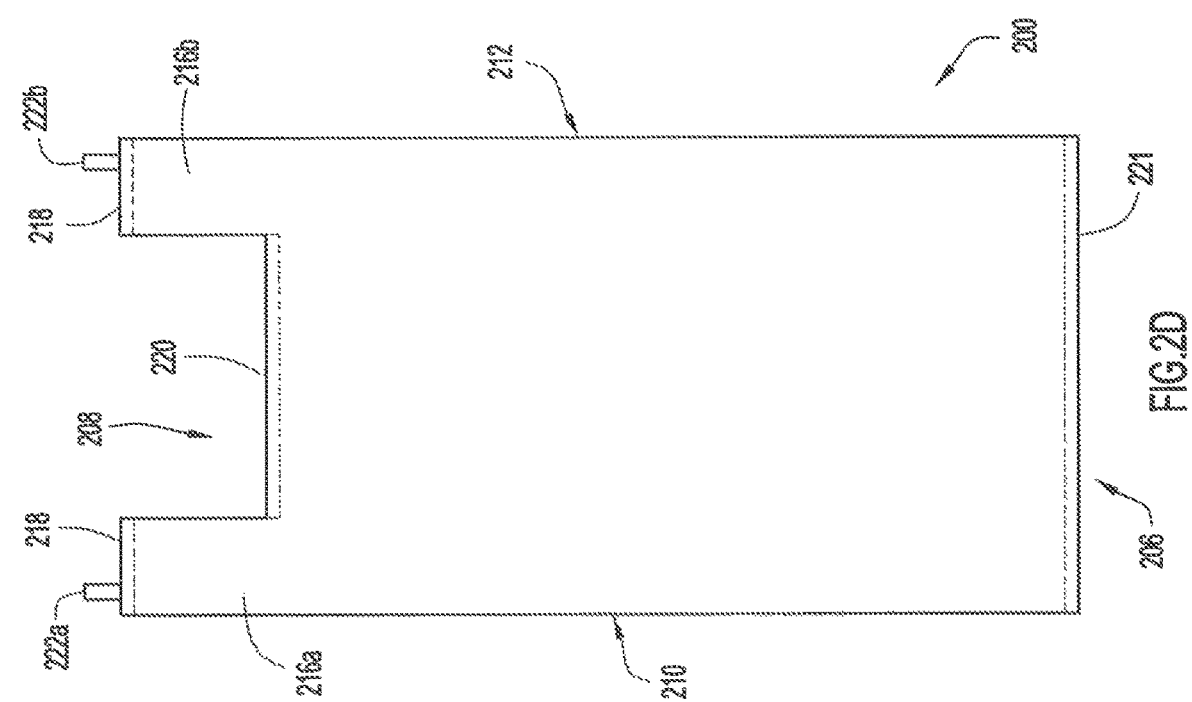
FIG. 2D is a bottom view in plan of the pack of liner sheets of FIGS. 2A and 2B.

Referring now to FIG. 2B, there is shown a top view illustrating the top side of the backing layer 204. In the preferred embodiment, a pair of locking pegs 240 is secured to the top side of the backing layer 204 adjacent pack leading edge 206 and a single locking peg 240 is secured to the top side of the backing layer adjacent pack inner edge 220. These locking pegs 240 are adapted to fit into and be retained by a collection of strategically placed locking receptacles (clips), such as locking receptacles 118 secured on the bore wall 104 of the exemplary MRI machine shown in FIG. 7. However, additional locking pegs may be secured at other locations to the top side of backing layer 204 as necessary. The locking pegs 240 adjacent the pack leading edge 221 and the pack inner edge 220 together with the strategically placed locking receptacles (clips) 118 on the MRI bore wall 104 function to guide the pack of liner sheets 200 into place inside the MRI bore, as well as hold the pack of liner sheets 200 substantially flush against the MRI bore wall.

Additionally, the preferred embodiment described above has a locking peg 240 secured to the top side backing layer of each flap 216a, 216b adjacent pack outer edge 218. These locking pegs cooperate with locking receptacles or clips secured to the front face of an MRI machine on each side the bore (e.g., clips 118 secured to the front face 120 of the exemplary MRI machine 100 shown in FIG. 7) to immobilize the pack of liner sheets 200 and allow for a simple release so that the pack 200 can be easily removed once all liner sheets are used. The locking receptacles (clips) 118 on the front face of the MRI machine have the same structural configuration as the locking receptacles (clips) 118 secured on the bore wall 104 of the exemplary MRI machine shown in FIG. 7, which are described in greater detail below.

After removal of an empty pack of liner sheets, a new liner pack may be inserted inside the MRI bore 104 utilizing the existing receptacles (clips) 118 in the MRI machine bore and the existing receptacles (clips) 118 on the front face of the MRI machine 100. The pack of multi-layered liner sheets 200 is designed to cover substantially the entirety of the curved portion of the MRI scanner bore 104, precisely following the bore curvature, as well as any bore angles.

Referring now to FIGS. 3A and 3B, further consideration is given to the structure of the locking pegs 240 and the locking receptacles or clips 118 (e.g., the receptacles or clips strategically positioned within the bore 104 and on the front surface 120 of the exemplary MRI machine 100 shown in FIG. 7) embodying the teachings of the present invention. As depicted in FIGS. 3A, 3B, locking pegs 240 on the leading end 206 of the backing layer 204 (as well as the other locking pegs illustrated in FIG. 2B, but not shown in FIG. 3A) include a base portion 241 and a T-shaped cross-section key 242 comprising a narrow stem 243 to which is attached a horizontally disposed locking lug 244. The key is attached to and extends upwardly from the base portion as best seen in FIG. 3B. As further depicted in FIGS. 3A and 3B, the locking receptacles or clips 118 comprise a generally square-shaped body having that top and bottom portions 118a, 118b, a rear portion 118c, a front portion 118d, and a pair of opposite side portions 118e defining a T-shaped cross-section keyway 122 disposed inwardly through the front portion 118d. The keyway has a narrow vertical opening 122a passing downwardly through the bottom portion 118b and an expanded horizontal slot 122b that is parallely aligned with top portion 118a.

As best seen in FIG. 3B, to secure the locking pegs 240 within the locking receptacles or clips 118, the T-shaped cross-section key 242 is passed into the keyway 122 and slidably moved therealong, thus guiding the locking lug 244 between the inner surfaces of the top and bottom portions 118a, 118b of the body. The locking key and the keyway are formed such that, when the key 242 is moved into the keyway 122, at least the top surface of the locking lug 244 slides in slight running contact with the adjacent inner surface of the flat top portion 118a to provide a close fit between the two surfaces. Sufficient sliding contact is maintained between the coacting surfaces to insure that locking pegs 240 and locking receptacles 118 remain locked together in assembly.

Alternatively, the locking pegs 240 and the locking clips 118 may both be formed of a non-metallic resilient material, such as a resilient polymer material, so that a slight interference fit can be provided between the key 242 and the keyway 122 to further insure that the two conjoined components remain locked together by fr tion when assembled. The polymer material may be any suitable MRI invisible material, such as Teflon® or polyethylene.

The backing layer 204 is formed from a sturdy material (i.e., a material sturdier than the material of the liner sheets, such as flexible cardboard or thin, flexible plastic, e.g., polyethylene, by which all liner sheets will be supported) to permit the pack 200, upon bending (contouring) of the backing layer 204, to generally conform to an MRI bore wall and prevent it from sagging (best seen in FIGS. 4A-6). Typically, each pack 200 is enclosed in a sterile package containing approximately ten to twenty liner sheets, depending on the size of the MRI bore. Due to limited space in the MRI bore, and for the comfort of patients, the pack of liner sheets 200 is designed to be as thin as possible. This limits the change in bore dimension within the MRI bore caused by the pack, therefore not limiting patient access to the bore due to patient habitus, i.e., different patient body shapes. The pack of liner sheets 200 is further designed to fit substantially flush and entirely within the dimensions of the MRI bore while taking into account the variations between different manufacturer designs and specifications.

Turning now to FIGS. 4A-7, the manner of securing the pack of multi-layered liner sheets 200 of FIGS. 2A and 2B in the bore 104 of the exemplary MRI machine 100 (shown in FIGS. 1 and 5-7) is illustrated. For purposes of clarity, pull tabs 222a, 222b have been omitted from FIGS. 4A, 4B, 5, and 6. Initially, an MRI operator (or other personnel) determines whether locking receptacles (clips) 118 (shown in FIG. 7 of exemplary MRI machine 100) have been previously installed on the MRI machine. If not, clips 118 appropriately designed for locking pegs 240 are strategically placed and secured inside the MRI bore 104, as well as on the front face 120 of the MRI machine (FIG. 7). Due to design differences for each brand of MRI scanner, startup packs of liners 200 will have their own templates to assist with the installation of the locking receptacles (clips) at the appropriate locations inside an MRI bore and on a front face of an MRI scanner (e.g., the exemplary MRI scanner 100 shown in FIG. 7).

After locking receptacles (clips) 118 are installed, an MRI operator takes a flat pack of liners 200 out of its sterile packaging and contours (flex or bend) the pack to a shape generally corresponding to the interior dimensions of the MRI bore 104 (FIG. 4A). As depicted in FIG. 4A, the pack 200 is contoured such that backing layer 204 with its attached pegs 240 face outward toward bore wall 104 and liner sheets 202 (not shown in FIG. 4A) face inward toward a patient (not shown) upon insertion of the pack inside MRI bore 102. However, prior to inserting pack 200 inside the MRI bore, flaps 216a, 216b are folded (bent) outwardly, as depicted by directional arrows A shown in FIG. 4B, to a position that is generally parallel to front face 120 of the exemplary MRI machine 100 shown in FIG. 5.

Thereafter, as depicted in FIGS. 5 and 6, the pack 200 is aligned in the MRI bore such that edges of pack sides 210, 212 are in alignment with sides 114, 116 of horizontal planar surface 106. Once aligned, contoured pack 200 is slid inside the MRI bore (FIG. 5), T-shaped cross-section keys 242 of locking pegs 240 on backing layer 204 are passed into keyways 122 of clips 118 attached to the MRI bore wall 104 and slidably moved therealong to guide the locking lug 244 between inner surfaces of top and bottom portions 118a, 118b to lock the conjoined components together in assembly.

After these components are locked together, flaps 216a, 216b are flexed slightly to permit T-shaped cross-section key 242 of locking pegs 240 on the top surface of the flaps (see FIG. 2B) to pass into keyway 122 of locking receptacles 118 on front face 120 of the MRI machine and to slidably move therealong to guide locking lug 244 between inner surfaces of top and bottom portions 118a, 118b to lock the conjoined components together in assembly. As mentioned previously, connecting the locking pegs 240 on flaps 216a, 216b to the receptacles 118 on front face 120 of the MRI machine, as depicted in FIG. 6, serves to immobilize the pack of liner sheets and allow for a simple release so pack 200 can be easily removed once all liner sheets are used.

Figure 8:
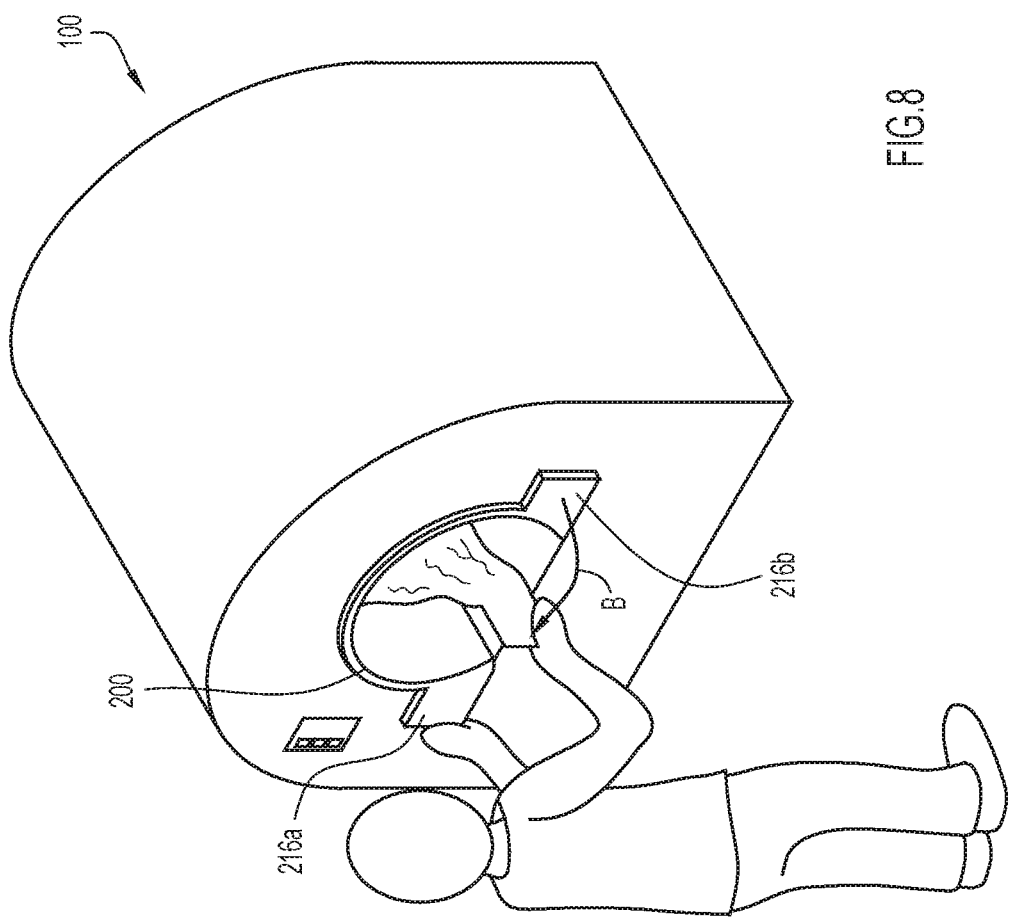
FIG. 8 is a view in perspective showing the pack of FIGS. 2A and 2B deployed in place in an exemplary MRI machine and a liner sheet being torn-away from the pack by an MRI operator according to an embodiment of the present invention.

Following each patient procedure (e.g., scan), the lowermost sheet in the pack 200 is pulled from the open front end 108 of the MRI bore 102 by an MRI operator (see exemplary MRI machine 100 shown in FIG. 8). As depicted by directional arrow B shown in FIG. 8, the MRI operator merely has to grasp pull tabs 222a, 222b (not shown in FIG. 8 for purposes of clarity) or flaps 216a, 216b and pull simultaneously laterally and outwardly to quickly and easily disconnect the lowermost sheet from the subsequent sheet in the pack, thereby leaving the subsequent sheet in place to face the next patient.

Figure 9:
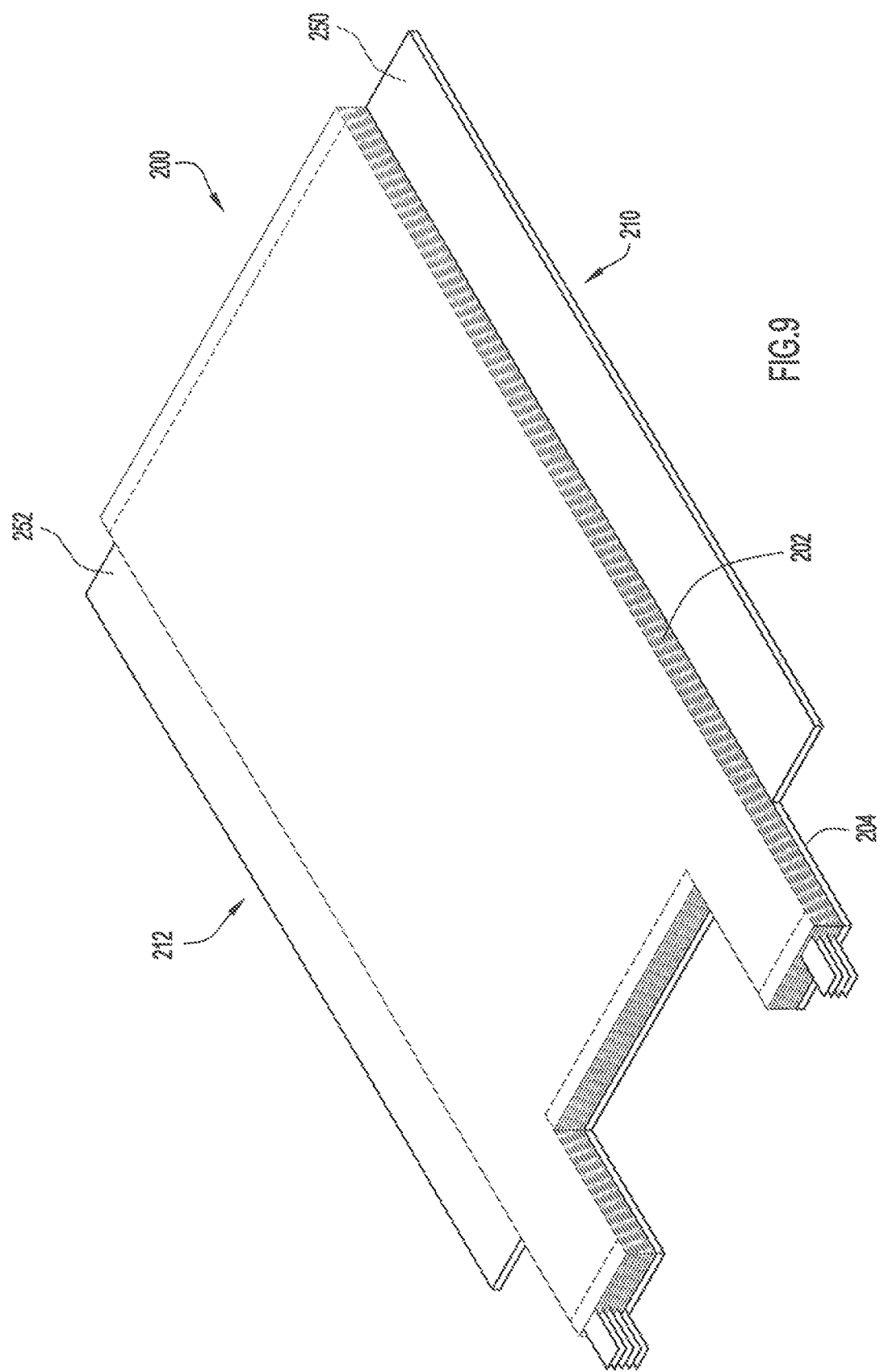
FIG. 9 is a bottom view in perspective of a pack of dispensable liner sheets according to an embodiment of the present invention illustrating a portion of the opposing sides of a backing layer extending laterally beyond the liner sheets.
Figure 10:
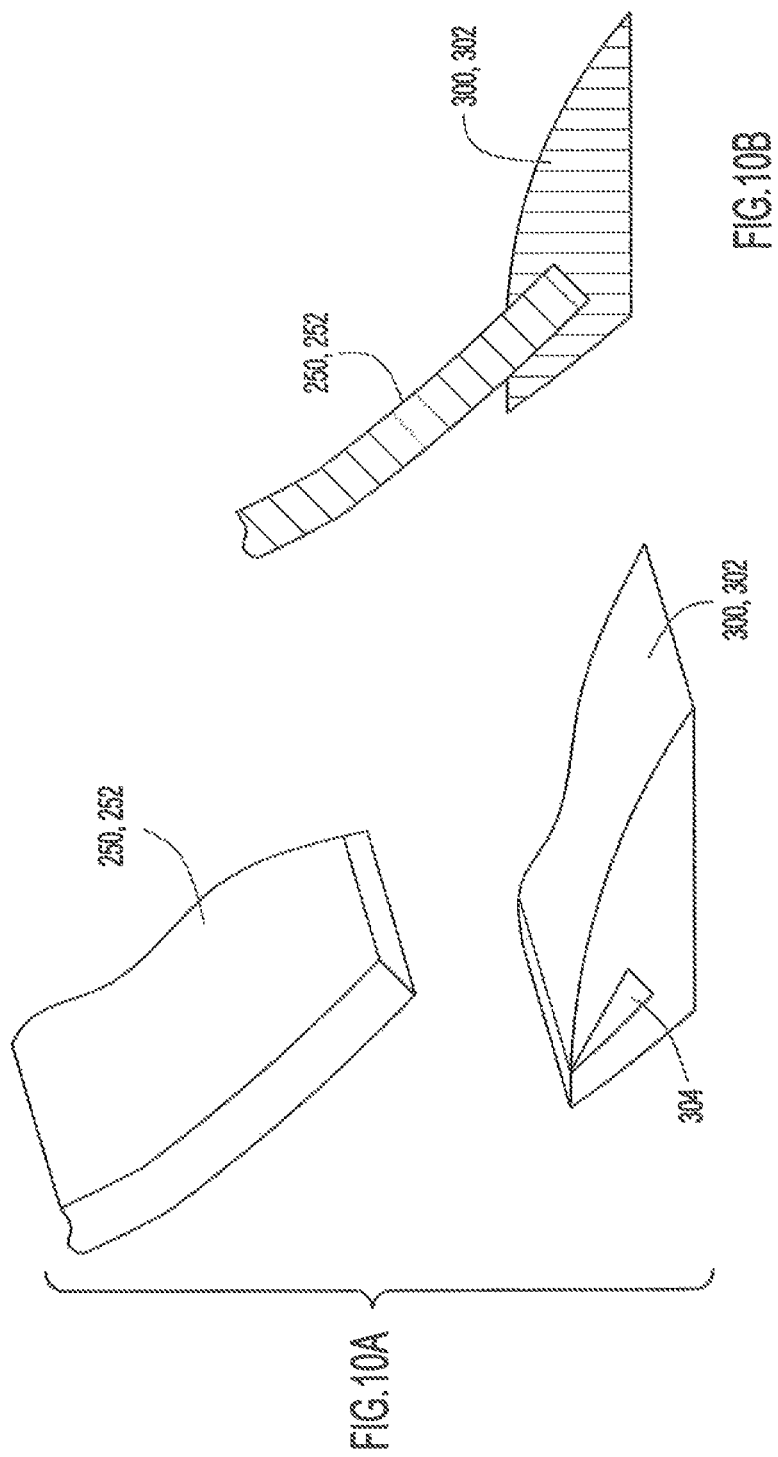
FIG. 10A is a fragmentary perspective view illustrating a laterally extending side portion of the backing layer of FIG. 9 and a guide rail for securing the pack inside a bore of an MRI machine.
FIG. 10B is a cross-sectional view illustrating the laterally extending side portion of the pack backing layer of FIG. 10A secured within a groove of the guide rail of FIG. 10A as it would appear when deployed in place in a bore of an MRI machine according to an embodiment the present invention.

Another embodiment of the invention, derived from the first embodiment (FIG. 2A), is depicted in FIG. 9. In this embodiment, the pack of liner sheets 200 has been modified in the following manner. First, instead of having locking pegs 240 secured to pack backing layer 204 adjacent the pack leading end 206, inner edge 220, and trailing edge 218, locking pegs 240 (not shown) are only secured to the pack backing layer adjacent the trailing edge 218 of flaps 216a, 216b. As described in the previous embodiment, locking pegs 240 cooperate with locking receptacles or clips 118 secured to the front face of an MRI machine on each side the bore (e.g., clips 118 secured to the front face 120 of the exemplary MRI machine 100 shown in FIG. 7) to immobilize the pack of liner sheets 200 and allow for a simple release so the pack 200 can be easily removed once all liner sheets are used. Second, a portion 250, 252 of the opposing sides of pack backing layer 204, generally referenced 210, 212 in FIG. 9, is extended laterally outward beyond the liner sheets 202. As shown in FIGS. 10A-12, the laterally extending side portions 250, 252 have longitudinally extending outer edges that are co-extensive with the pack and cooperate with elongated guide rails 300, 302 adapted to be affixed inside an MRI bore to facilitate installation of the pack of liner sheets 200 inside the bore.

As depicted in FIGS. 10A and 10B, each guide rail 300, 302, which may be formed of suitable non-metallic material, e.g., a polymer material, has defined therein a groove 304 that preferably extends the entire length of the guide rail. The grooves 304 have a configuration to slidably receive the longitudinally extending edges of the laterally extending portions 250, 252 to securely maintain the pack of liner sheets 200 in its contoured (curved) configuration inside the MRI bore and substantially flush against the non-linear wall portion 104 of the MRI bore 102. It is preferred, however, that the guide rails 300, 302 be formed of a resilient non-metallic material, such as a resilient plastic or rubber material, so that the guide rail grooves 304, when the longitudinal edges of the side portions 250, 252 are slidably received in the grooves, will expand slightly to conform to the shape of the edges, thereby providing a sight interference fit to further insure that the conjoined parts remain locked together by friction when assembled. Just the same, however, any other suitable material known in the art may be employed to form the guide rails 300, 302.

Figure 11:
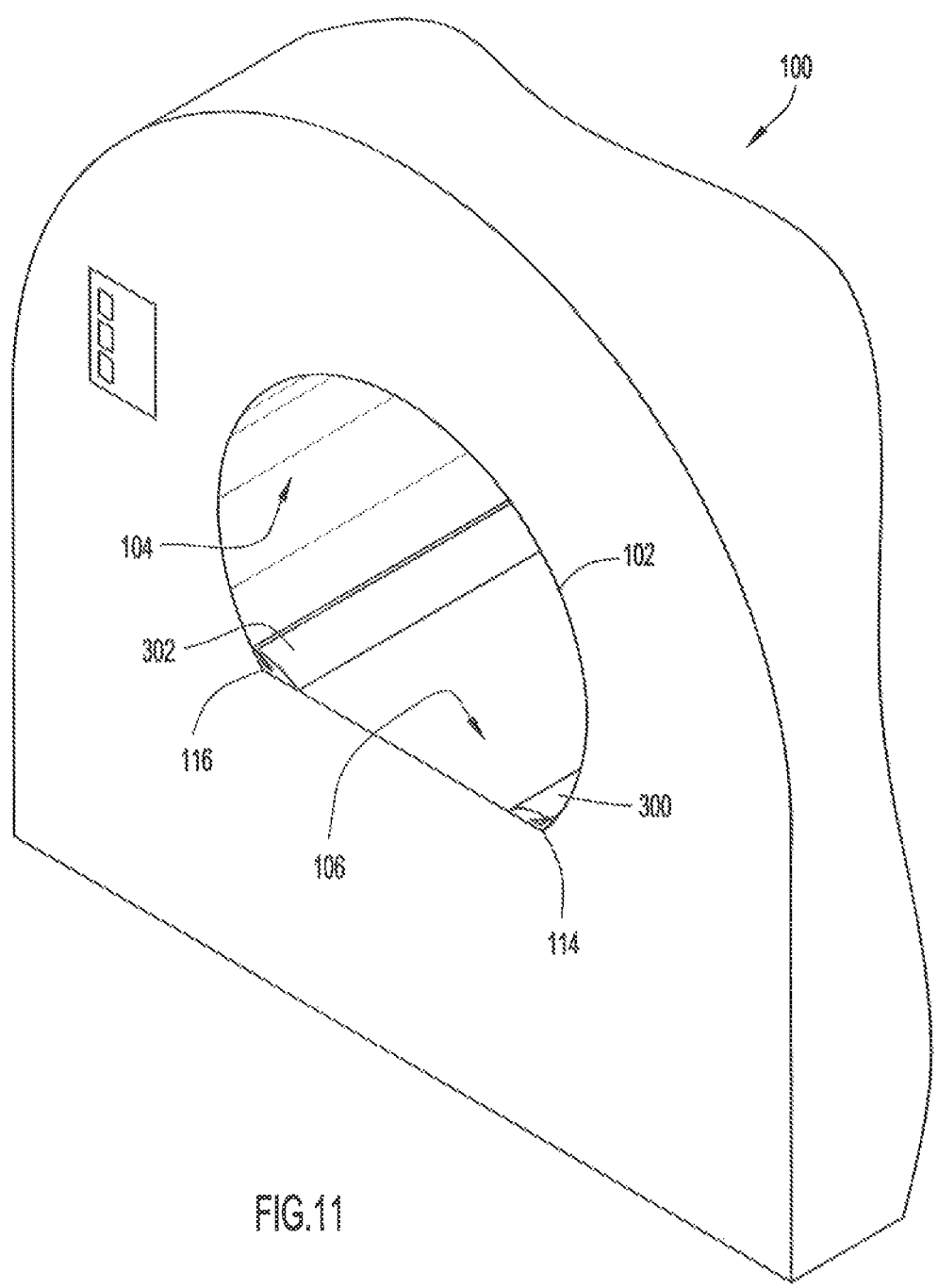
FIG. 11 is a front perspective from above, left, illustrating two guide rails of FIG. 10A affixed within a bore of an MRI machine according to an embodiment of the present invention.
Figure 12:
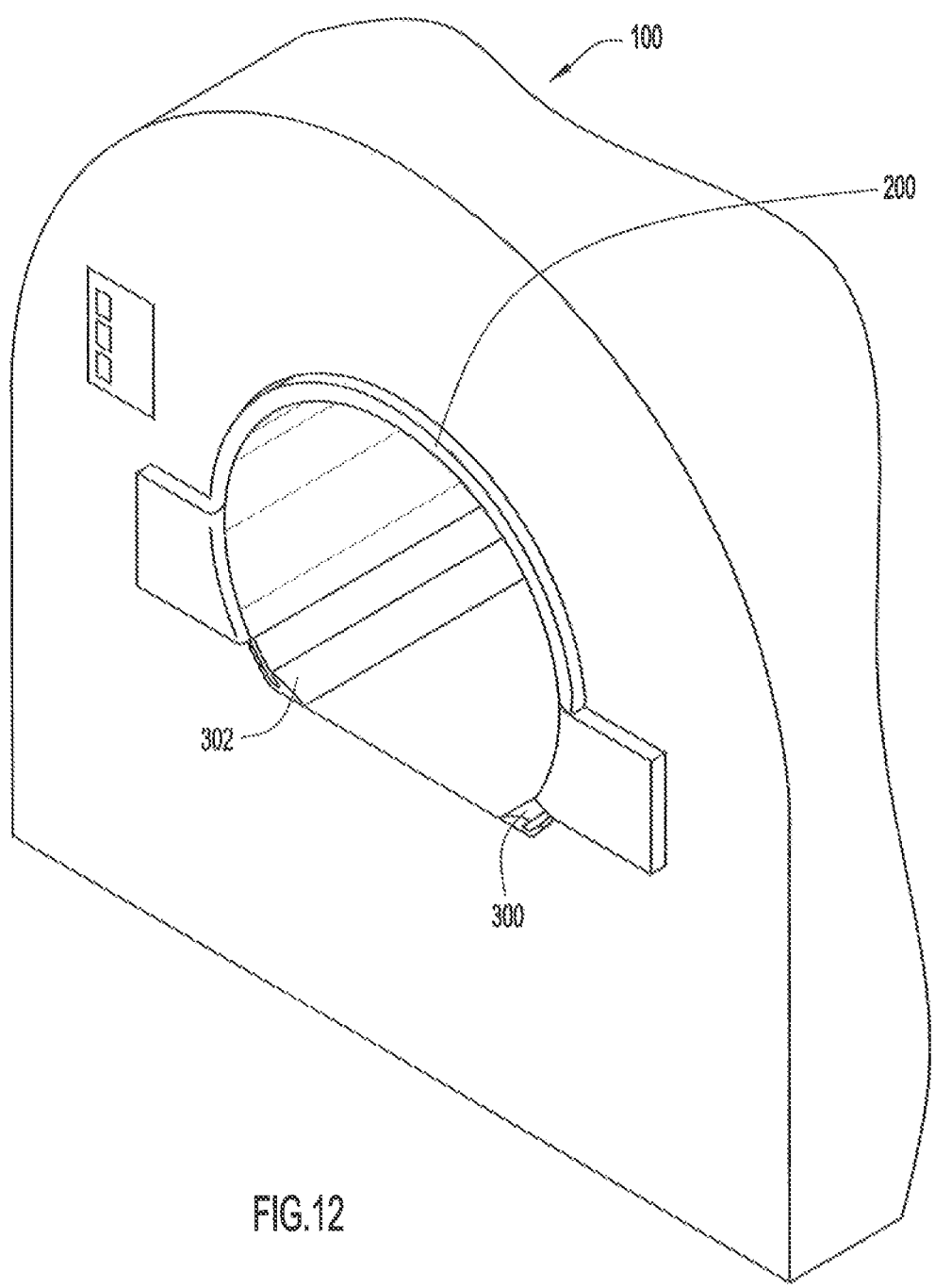
FIG. 12 is a front perspective from above, left, illustrating the pack of FIG. 9 secured inside a bore of an MRI machine by the guide rails of FIG. 11 in accordance with an embodiment of the present invention.

Referring to FIGS. 11 and 12, the guide rails are shown affixed inside MRI bore 102 of exemplary MRI machine 100 at the junction of opposing sides 114, 116 of planar horizontal surface 106 and the non-linear bore wall surface (arcuate or curved surface) 104 of the MRI bore 102 (see exemplary MRI machine 100 shown in FIG. 11). The guide rails 300, 302 may be affixed to surfaces 104 and 106 by suitable adhesives or mechanical fasteners (e.g., epoxy or screws). However, any other suitable mounting means known in the art may be employed. The guide rails preferably extend from the open front end 108 to the open rear end 110 of the MRI bore 102 to help guide the pack of liner sheets 200 to fit in place and hold the pack of liner sheets in its contoured (curved) configuration substantially flush against the non-linear wall portion 104 of the exemplary MRI machine 100 as depicted in FIG. 12.

Figure 13:
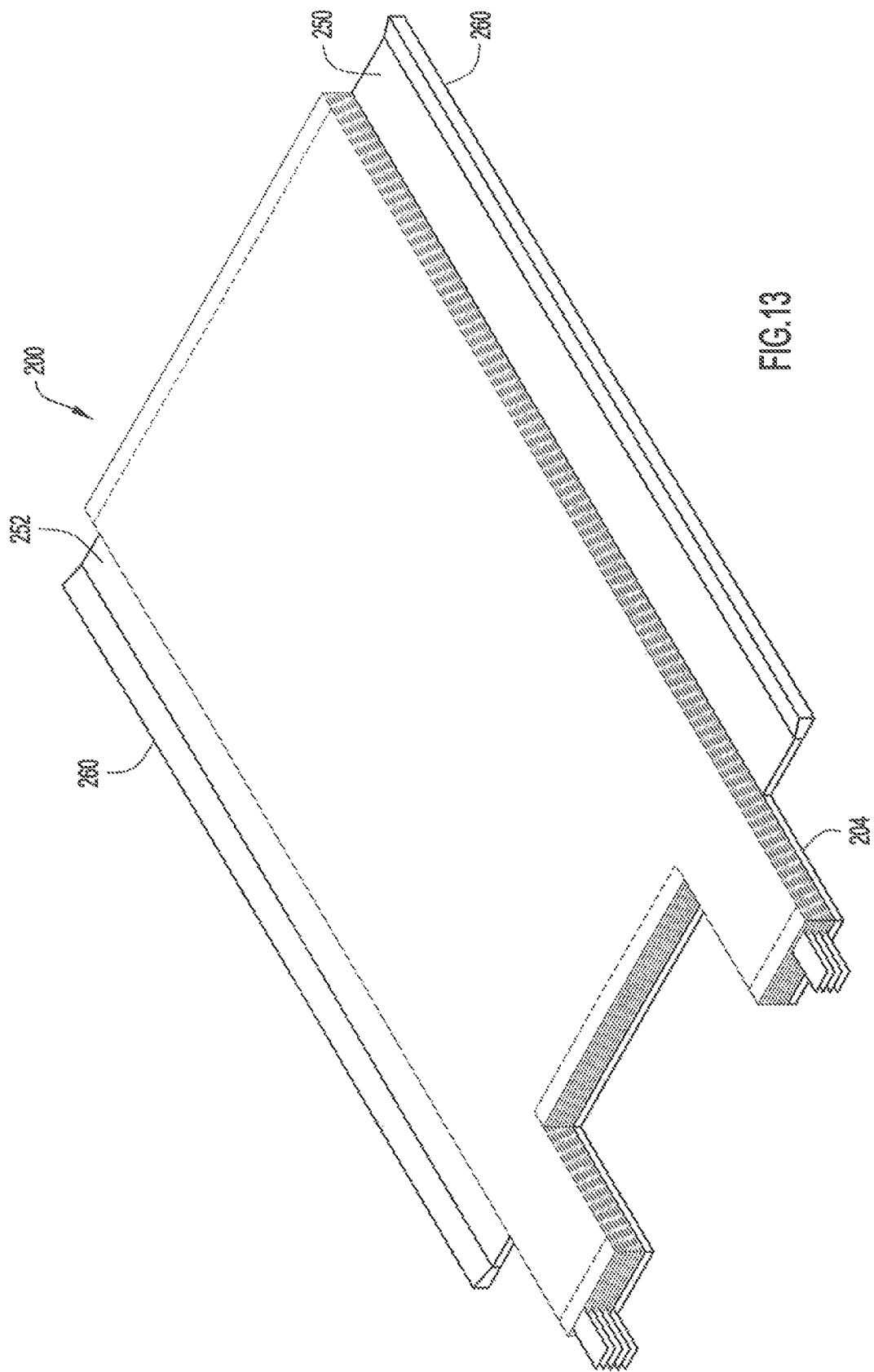
FIG. 13 is a bottom view in perspective of a pack of dispensable liner sheets similar to the pack of FIG. 9 illustrating the opposed laterally extending side portions of the pack backing layer with a contour-shaped insert attached thereto in accordance with a further embodiment of the present invention.

Turning now to FIG. 13, there is shown another embodiment of the present invention derived from the second embodiment (FIG. 9). In this embodiment, the pack of liner sheets 200 is of similar construction to the pack of liner sheets depicted in FIG. 9, thus like parts are identified with like reference numbers. However, the pack of liner sheets 200 differs from the pack of liner sheets depicted in FIG. 9 in that an insert 260 having a contoured shape is attached to an edge of the laterally extending side portions 250, 252 of pack backing layer 204. The inserts 260 may be formed from molded polymeric MRI transparent material, such as plastic, e.g., polyethylene, and attached to the side portions 250, 252 by an adhesive. Alternatively, the inserts 260 may simply be a section of the laterally extending side portions 250, 252 folded about a score line set back from the longitudinal edges of the side portions 250, 252. Each score line extends the length of the side portions and functions in a manner similar to a living hinge. The score lines may be formed in the laterally extending side portions 250, 252 of backing layer 204 using techniques well know to one skilled in the art.

The inserts 260 cooperate with elongated guide rails 310, 312 adapted to be affixed inside an MRI bore in a similar manner as guide rails 300, 302 to facilitate installation of the pack of liner sheets 200 inside the bore (see FIGS. 14A-16). As depicted in FIGS. 14A, 14B, each guide rail 310, 312 has a contour-shaped groove 314 that preferably extends the entire length of the guide rail. The contour-shaped inserts 260 and the contour-shaped grooves 314 have complementary configurations. The grooves 314 slidably receive the inserts 260 to securely maintain the pack of liner sheets 200 in its curved configuration inside the MRI bore and substantially flush against the non-linear wall portion 104 of the MRI bore 102. Moreover, the complementary configurations of the contour-shaped inserts 260 and contour-shaped grooves 314 help to securely maintain the pack of liner sheets 200 locked within the grooves to prevent inadvertent disengagement of the conjoined parts when assembled.

Figure 15:
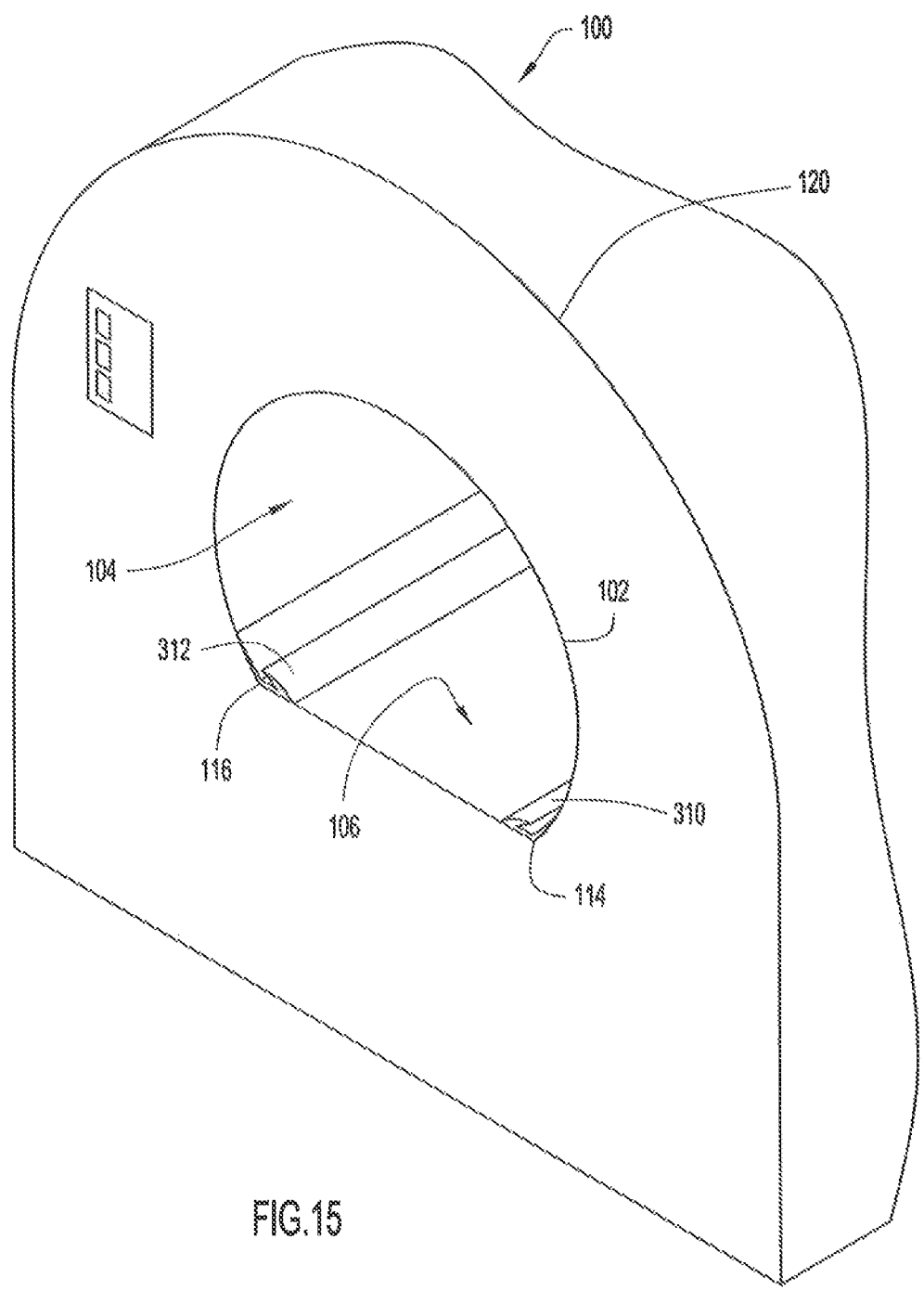
FIG. 15 is a front perspective from above, left, illustrating two guide rails of FIG. 14A affixed within a bore of an exemplary MRI machine according to an embodiment of the present invention.
Figure 16:
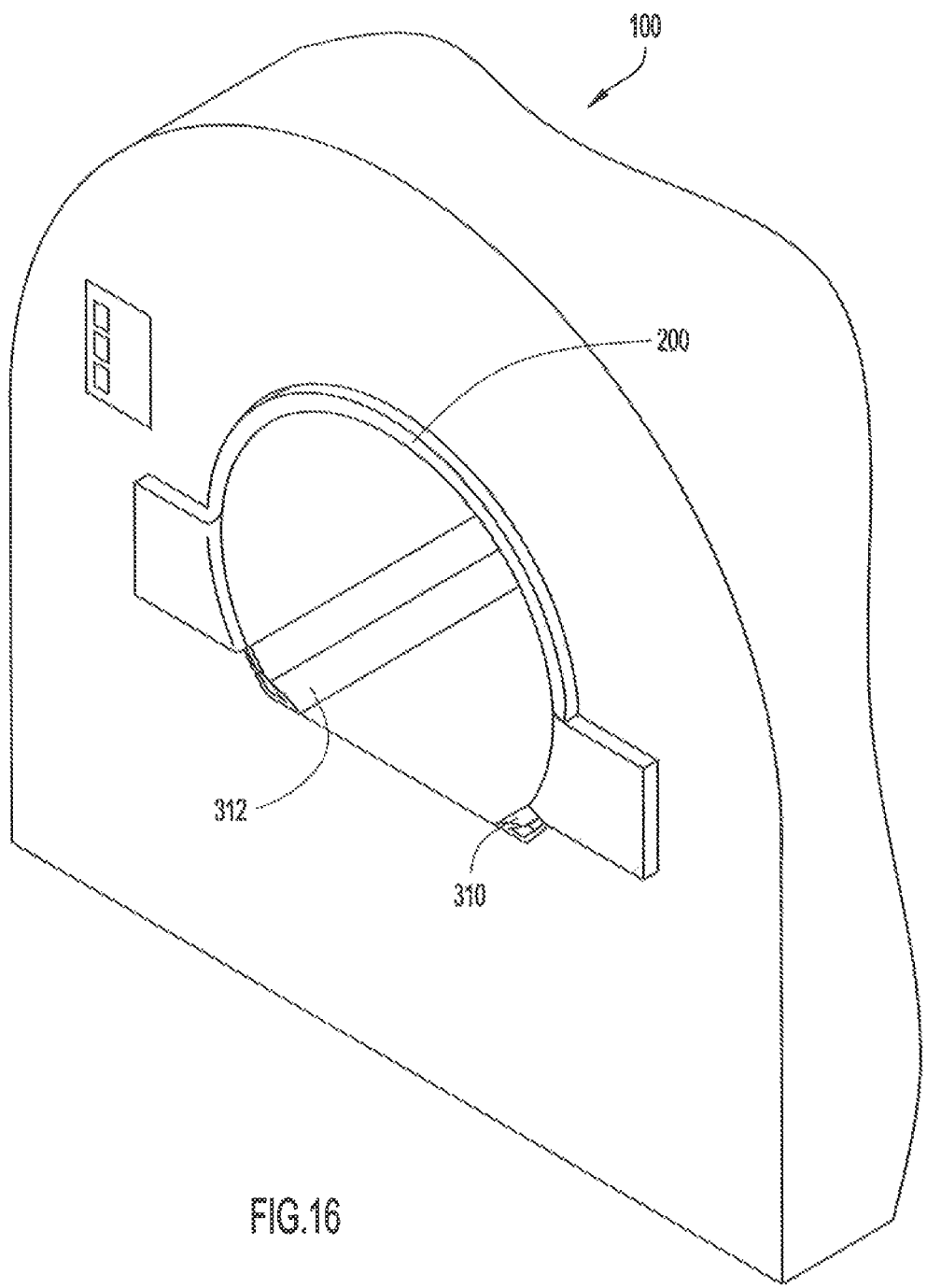
FIG. 16 is a front perspective from above, left, illustrating the pack of FIG. 13 secured inside a bore of an exemplary MRI machine by the guide rails of FIG. 15 in accordance with an embodiment of the present invention.

Referring to FIGS. 15 and 16, guide rails 310, 312 are shown affixed inside MRI bore 102 of exemplary MRI machine 100 at the junction of opposing sides 114, 116 of planar horizontal surface 106 and the non-linear bore wall surface (arcuate or curved surface) 104 of the MRI bore 102 (see exemplary MRI machine 100 shown in FIG. 15). Similar to guide rails 300, 302 depicted in FIG. 11, guide rails 310, 312 may be affixed to surfaces 104 and 106 by suitable adhesives or mechanical fasteners (e.g., epoxy or screws). However, any other suitable mounting means known in the art may be employed. The guide rails preferably extend from the open front end 108 to the open rear end 110 of the MRI bore 102 to help guide the pack of liner sheets 200 to fit in place and hold the pack of liner sheets in its contoured (curved) configuration substantially flush against the non-linear wall portion 104 of the exemplary MRI machine 100 as depicted in FIG. 16.

The manner of securing the modified packs of liner sheets 200 depicted in FIGS. 9 and 13 will now be described in detail. First, an MRI operator (or other personnel) positions the guide rails 300, 302 (FIG. 9) or the guide rails 310, 312 (FIG. 10) inside the MRI bore at the junction of opposing sides 114, 116 of planar horizontal surface 106 and the non-linear bore wall surface (arcuate or curved surface) 104 of the MRI bore 102 (see exemplary MRI machine 100 shown in FIGS. 11 and 15). Thereafter, guide rails 300, 302 or 310, 312 (depending on which pack design is selected) are affixed to surfaces 104, 106 by suitable adhesives or mechanical fasteners (e.g., epoxy or screws).

Next, an MRI operator (or other personnel) determines if locking receptacles (clips) 118 (shown, for example, in FIG. 7) have been previously installed on the front face 120 of the MRI machine. If not, locking clips 118 appropriately designed for locking pegs 240 on flaps 216a, 216b of modified packs 200 are secured to front face 120 of the MRI machine (FIG. 7). Since each brand of MRI scanner typically has a different design, startup packs of liners 200 will have templates to assist with the installation of locking receptacles (clips) 118 at the appropriate locations on the front face of an MRI scanner (e.g., the exemplary MRI scanner 100 shown in FIG. 7).

After locking receptacles (clips) 118 are installed, an MRI operator (or other personnel) takes a modified flat pack of liners 200 out of its sterile packing, and contours (flexes or bends) the pack to a shape generally corresponding to the interior dimensions of the MRI bore 104. See, for example, the contouring of pack 200 in FIG. 4A. As depicted for the pack shown in FIG. 4A, the modified pack 200 of either FIG. 9 or FIG. 13 is contoured such that backing layer 204 faces outward toward bore wall 104 and the stack of liner sheets 202 faces inward toward a patient (not shown) upon insertion of the pack inside MRI bore 102. However, prior to inserting modified pack 200 inside the MRI bore, flaps 216a, 216b are folded (bent) outwardly (as depicted by directional arrows A shown in FIG. 4B for non-modified pack 200) to a position that will be generally parallel to front face 120 of the exemplary MRI machine 100 shown in FIG. 5.

Next, the selected modified pack 200 is aligned with the front open end 108 of the MRI bore such that edges of the laterally extending portions 250, 252 or the contoured inserts 260 are slidably received in grooves 304 or 314 of the guide rails. Once the edges or inserts are received in the grooves, modified pack 200 is slid toward the open rear end 110 of the MRI bore until the entire exposed bore wall surface 104 is covered by the pack of liners.

After these components are conjoined, flaps 216a, 216b are flexed slightly to permit T-shaped cross-section key 242 of locking pegs 240 (shown in FIG. 2B) to pass into keyway 122 of locking receptacle 118 on front face 120 of the MRI machine and to slidably move therealong to guide the locking lug 244 between inner surfaces of top and bottom portions 118a, 118b to lock these components together in assembly. As previously stated, locking pegs 240 on flaps 216a, 216b to receptacles 118 on the front face 120 of the MRI machine, as depicted in FIG. 6, serves to immobilize the liner sheets and allow for a simple release so modified pack 200 can be easily removed once all liner sheets are used.

Following each patient procedure (scan), the lowermost sheet in the modified pack 200 is pulled from the open front end 108 of the MRI bore 102 by an MRI operator (see exemplary MRI machine 100 shown in FIG. 8). As depicted by directional arrow B shown in FIG. 8, the MRI operator merely has to grasp pull tabs 222a, 222b (not shown in FIG. 8 for purposes of clarity) or flaps 216a, 216b and pull simultaneously outwardly and laterally to quickly and easily disconnect the lowermost sheet from the subsequent sheet in the pack, thereby leaving the subsequent sheet in place to face the next patient.

With infection control being a standard in medical institutions, this invention permits a healthcare institution to maintain a sanitary MRI machine environment with one quick and easy step. Unlike current standards of cleaning MRI bores out with harsh chemicals which take time to air out between patients, or lining the MRI bore with a sterile plastic sheet in the form of a cylindrical sleeve after each patient procedure (scan) which takes time to install, this invention takes mere seconds with no lingering harsh chemical fumes to irritate patients eyes and respiratory tract and no extensive MRI machine down time while replacement plastic sheets are installed.

While it is known to use a sterile plastic drape in the form of a cylindrical sleeve to provide a sterile environment in the bore of a scan machine such as an MRI scanner during a scan procedure, as shown in U.S. Patent Application Publication Pub. Nos. 2003/0181810 (Murphy et al.), 2006/0079748 (Murphy et al.), 2008/0216844 (Olfert et al.), and 2013/0092177 (Chua et al.), each sterile drape in the Murphy et al., Olfert et al. and Chua et al. systems is separately packaged, and considerable time is involved in unpacking each new drape and then installing it in the scanner for each surgical procedure. There is no suggestion in Murphy et al., Olfert et al. or Chua et al. of providing a dispenser for plural liner sheets, particularly in the form of a pack of serially connected liner sheets as provided by the present invention.

The present invention is designed to protect successive scan patients from contaminants by enabling the tearing away of contaminated liner sheets from a pack of such sheets and exposing a fresh clean liner sheet for each successive patient. This invention as described is a pack of disposable multi-layered liner sheets suited for covering the interior bore wall of MRI scanners or any other medical scanner having a long, hard to clean, tunnel. The invention is comprised of a dispenser pack of multiple tear-away liner sheets used to maintain a clean and sanitary environment between each patient scan. Each individual sheet creates a new clean physical barrier between a patient and the scanner interior wall to guard against a patient's physical contact with the MRI scanner as well as guarding against airborne particles from coughing or sneezing patients that can collect on the MRI interior bore wall.

While only specific combinations of the various features and components of the present invention have been discussed herein, it will be apparent to those of skill in the art that desired subsets of the disclosed features and components and/or alternative combinations of these features and components can be utilized, as desired. For example, (1) variations in pack designs may be provided to compensate for items such as vent openings, lighting strips, and user interfaces (keypads), etc.; (2) liner sheets may be utilized that not only line the entire bore of scanner, but extend out of the front opening of the scanner bore to help smoothly guide patients inside the bore without tearing or damaging multiple liners in the pack; (3) the keyway of the locking receptacles (clips) attached at the rear of the scanner bore may be slightly inclined to pull the pack of liner sheets upward to assure the pack sits flush with the bore wall; and (4) relaxing themes may be printed on the liner sheets to help alleviate anxieties of claustrophobia in patients.

Additionally, refills may be attached to the MRI bore wall with hook and loop type fasteners (such as Velcro®) placed at strategic anchoring points throughout the bore. Every scanner may have a setup template included with the initial startup pack of liners displaying the strategic anchoring points for the hook and loop fasteners. Should Velcro® fasteners be used, the pack of liner sheets may be designed so that the last sheet in the pack will tear the pack away from the Velcro® fasteners affixed to the bore wall of the scanner so that a refill pack of liners may be quickly attached thereto.

Having described preferred embodiments of a new and improved pack of disposable multi-layered liner sheets suitable for covering the interior bore wall of medical scanners having a long, hard to clean, bore or tunnel, particularly MRI scanners, and improved apparatus and methods for covering the interior bore wall of medical scanners, particularly MRI scanners, to establish and maintain a sterile filed around a patient during a medical procedure or scan, it is believed that other modifications, variations, and changes will be suggested to those skilled in the art in view of the teachings set forth herein. It is therefore to be understood that all such variations, modifications, and changes are believed to fall within the scope of the invention as defined by the appended claims. Although specific terms are employed herein, they are used in a generic and descriptive sense only and not for purposes of limitation.

What is claimed is:

1. A liner pack for mounting on a medical device having a bore with a curved bore wall surface and an open front end, the liner pack comprising:
    a backing layer having a top side and a bottom side;
    a stack of disposable multi-layered liner sheets secured to the bottom side of the backing layer; and mounting means for supporting the liner pack within the bore in a generally curved configuration to substantially cover the bore wall surface, wherein the stack of disposable multi-layered liner sheets comprises a series of end-to-end connected sheets which are configured to conform to and cover the curved bore wall surface substantially in its entirety, and wherein each sheet of the series of end-to-end connected liner sheets is removably attached at a leading end to a leading end of respective succeeding and preceding liner sheets in the stack by a straight line of perforations and at a trailing end to a trailing end of respective succeeding and preceding liner sheets in the stack by an adhesive.

2. The liner pack of claim 1, wherein the mounting means comprises attachment devices on the top side of the backing layer configured to cooperate with locking receptacles strategically secured to the curved bore wall surface to support the liner pack substantially flush against the bore wall surface in its generally curved configuration.

3. The liner pack of claim 2,
wherein the liner pack has a leading end and a trailing end; and
wherein the attachment devices are positioned on the top side of the backing layer adjacent the leading end and the trailing end of the liner pack.

4. The liner pack of claim 2,
wherein the backing layer has a leading end and a trailing end,
wherein the trailing end has a notch-shaped indentation extending inwardly from a trailing end outer edge to a trailing end inner edge, and
wherein the attachment devices are positioned on the top side of the backing layer adjacent an edge of the leading end and adjacent the outer and inner edges of the trailing end.

5. The liner pack of claim 1,
wherein the backing layer has a trailing end which includes a notch-shaped indentation extending inwardly from a trailing end outer edge to a trailing end inner edge, and
wherein segments of the trailing end on opposite sides of the indentation define a pair of opposing flaps extending from the inner edge to the outer edge and configured to engage a front face of the medical device adjacent the open front end of the bore.

6. The liner pack of claim 5,
wherein the mounting means comprises an attachment device secured to a top side of each flap adjacent its outer edge and configured to cooperate with a locking receptacle strategically attached to a front face of the medical device adjacent the open front end of the bore.

7. The liner pack of claim 1,
wherein the backing layer comprises a trailing end and a pair of opposing flaps extending outwardly from the trailing end, and
wherein the mounting means comprises a locking device attached to a top surface of each backing layer flap to engage a front face of the medical device adjacent the open front end of the bore to immobilize the pack of liner sheets.

8. A liner pack for mounting on a medical device having a bore with a curved bore wall surface and an open front end, the liner pack comprising:

a backing layer having a top side and a bottom side;
a stack of disposable multi-layered liner sheets secured to the bottom side of the backing layer; and
mounting means for supporting the liner pack within the bore in a generally curved configuration to substantially cover the bore wall surface, wherein the mounting means comprises attachment devices on the top side of the backing layer configured to cooperate with locking receptacles strategically secured to the curved bore wall surface to support the liner pack substantially flush against the bore wall surface in its generally curved configuration, wherein the attachment devices comprise locking pegs having a T-shaped cross-section key extending upwardly from a base portion; and wherein the locking receptacles comprise a body having a T-shaped cross-section keyway disposed inwardly through a front portion of body, the T-shaped cross-section keyway having a shape complementary to the T-shaped cross-section key to slidably receive the key such that the locking pegs and the locking receptacles remain locked together in assembly.

9. The liner pack of claim 8,
wherein the T-shaped cross-section key of the attachment devices includes a horizontally extending locking lug portion and the body of the locking receptacles includes top and bottom portions having inner surfaces; and
wherein the locking lug portion is slidably received between the inner surfaces of the top and bottom portions to provide an interference fit locking the attachment devices and the locking receptacles together by friction when assembled.

10. The liner pack of claim 8, wherein the stack of disposable multi-layered liner sheets comprises a series of end-to-end connected sheets which are configured to conform to and cover the curved bore wall surface substantially in its entirety.

11. The liner pack of claim 10, wherein each sheet of the series of end-to-end connected liner sheets is removably attached at a leading end and a trailing end to a leading end and a trailing end of respective succeeding and preceding liner sheets in the stack by an adhesive.

12. The liner pack of claim 11, wherein the adhesive is a low-tack releasable pressure sensitive adhesive positioned on a portion of an upper or lower surface of each sheet adjacent an edge of the leading end and the trailing end.

13. The liner pack of claim 10, wherein each sheet of the series of end-to-end connected liner sheets is removably attached at a leading end to a leading end of respective succeeding and preceding liner sheets in the stack by a straight line of perforations and at a trailing end to a trailing end of respective succeeding and preceding liner sheets in the stack by an adhesive.

14. The liner pack of claim 8, wherein the stack of disposable multi-layered liner sheets comprises a series of end-to-end connected sheets folded onto one another which are configured to conform to and substantially cover the curved bore wall surface in its entirety.

15. The liner pack of claim 14,
wherein each liner sheet has a leading end including an edge and a trailing end including an edge, and
wherein each liner sheet is removably attached at its leading end edge and its trailing end edge to a leading end edge and a trailing end edge of respective succeeding and preceding sheets in the stack by transversely extending linear perforations.

16. A liner pack for mounting on a medical device having a bore with a curved bore wall surface and an open front end, the liner pack comprising:
- a backing layer having a top side and a bottom side;
- a stack of disposable multi-layered liner sheets secured to the bottom side of the backing layer; and
- mounting means for supporting the liner pack within the bore in a generally curved configuration to substantially cover the bore wall surface,
- wherein each liner sheet in the stack has a trailing end and a pair of opposing flaps extending outwardly from the trailing end, the opposing flaps having an outer edge, and
- wherein the flaps include a pull tab extending outwardly from the outer edge of the flaps to permit an individual liner sheet to be separated from an underlying sheet in the stack of liner sheets.

17. The liner pack of claim 16, wherein the pull tabs extend outwardly from every other flap in an alternating sequence.

18. The liner pack of claim 1, wherein the multi-layered liner sheets each comprise a substrate selected from the group consisting of a layer of liquid absorbing material backed with a layer of liquid impervious material and a layer of liquid impervious material sandwiched between two layers of liquid absorbing material.

19. A liner pack for mounting on a medical device having a bore with a curved bore wall surface and an open front end, the liner pack comprising:
- a backing layer having a top side and a bottom side;
- a stack of disposable multi-layered liner sheets secured to the bottom side of the backing layer; and
- mounting means for supporting the liner pack within the bore in a generally curved configuration to substantially cover the bore wall surface,
- wherein the backing layer further includes opposing side portions laterally extending outward beyond the liner sheets, and
- wherein the mounting means comprises longitudinally extending outer edges of the side portions that are co-extensive with the pack and cooperate with grooves defined in elongated guide rails adapted to be affixed inside the bore to support the liner pack substantially flush against the bore wall surface in its generally curved configuration.

20. A liner pack for mounting on a medical device having a bore with a curved bore wall surface and an open front end, the liner pack comprising:
- a backing layer having a top side and a bottom side;
- a stack of disposable multi-layered liner sheets secured to the bottom side of the backing layer; and
- mounting means for supporting the liner pack within the bore in a generally curved configuration to substantially cover the bore wall surface,
- wherein the backing layer further includes opposing side portions laterally extending outward beyond the liner sheets, each side portion having a longitudinally extending outer edge substantially co-extensive with the pack, and
- wherein the mounting means comprises a contour-shaped insert attached at the longitudinally extending outer edge that cooperates with complementary contour-shaped grooves defined in elongated guide rails adapted to be affixed inside the bore to support the liner pack substantially flush against the bore wall surface in its generally curved configuration.

21. A method of covering a curved bore wall surface of a medical device having a bore defined therein which extends from a front face to a rear face of the device to maintain a sterile environment, the method comprising:
- providing a sterile liner pack including a backing layer having a top side and a bottom side, a stack of disposable multi-layered liner sheets secured to the bottom side, and mounting means for supporting the liner pack within the bore in a generally curved configuration to substantially cover the bore wall surface;
- securing locking receptacles adapted to cooperate with the mounting means to the curved bore wall surface at strategic locations to hold the liner pack substantially flush against the bore wall surface in its generally curved configuration;
- contouring the liner pack prior to insertion inside the bore to a shape generally corresponding to the curved bore wall surface; and
- inserting the contoured liner pack inside the bore toward the rear face of the device such that the mounting means engage the locking receptacles secured to the curved bore wall surface to hold the liner pack substantially flush against the bore wall surface in its generally curved configuration,
- wherein the mounting means comprises a plurality of locking pegs on the top side of the pack backing layer, each having a T-shaped cross-section key, and the locking receptacles secured to the bore wall surface each comprises a body having a complementary T-shaped section-section keyway, and
- wherein inserting the contoured pack toward the rear face of the device further comprises slidably receiving the T-shaped cross-section keys in the T-shaped cross section keyways to lock the locking pegs and the locking receptacles together in assembly to hold the liner pack substantially flush against the bore wall surface in its generally curved configuration.

22. The method of claim 21,
- wherein the liner pack has opposed flaps substantially co-extensive with the backing layer extending outwardly from a trailing end of the pack, the front face of the medical device has locking receptacles secured adjacent the bore, and the mounting means further comprises a locking peg on a top side of each flap, and
- wherein inserting the contoured pack toward the rear face of the device further comprises:
- folding the flaps outwardly to a position generally parallel to the front face, and
- slidably receiving the locking pegs within the locking receptacles to immobilize the liner sheets and allow for release of the pack once all liner sheets are used.

23. The method of claim 21,
- wherein bore of the medical device has an open front end and the stack of disposable multi-layered liner sheets secured to the bottom side of the backing layer comprises a series of end-to-end connected sheets having a leading end, each sheet of the series being removably attached at a leading end to a leading end of respective succeeding and preceding liner sheets in the stack by a straight line of perforations, and
- wherein the method further comprises:
- disconnecting a lowermost liner sheet from a subsequent sheet in the stack by tearing away the lowermost sheet from the stack via said line of perforations, and
- pulling the lowermost sheet outwardly through the open front end of the bore.

24. A method of covering a curved bore wall surface of a medical device having a bore defined therein which extends from a front face to a rear face of the device to maintain a sterile environment, the method comprising:

provperforming a sterile liner pack including a backing layer having a top side and a bottom side, a stack of disposable multi-layered liner sheets secured to the bottom side, and mounting means for supporting the liner pack within the bore in a generally curved configuration to substantially cover the bore wall surface;

securing locking receptacles adapted to cooperate with the mounting means to the curved bore wall surface at strategic locations to hold the liner pack substantially flush against the bore wall surface in its generally curved configuration;

contouring the liner pack prior to insertion inside the bore to a shape generally corresponding to the curved bore wall surface; and inserting the contoured liner pack inside the bore toward the rear face of the device such that the mounting means engage the locking receptacles secured to the curved bore wall surface to hold the liner pack substantially flush against the bore wall surface in its generally curved configuration, wherein the pack backing layer has opposed sides, the mounting means comprises a portion of the opposed sides extending laterally outward beyond the liner sheets, and the locking receptacles comprise elongated guide rails having a groove configured to receive longitudinally extending edges of the opposed laterally extending portions, and wherein inserting the contoured pack toward the rear face of the device further comprises slidably receiving the longitudinally extending edges in the grooves of the elongated guide rails to securely retain the edges within the grooves to hold the liner pack substantially flush against the bore wall surface in its generally curved configuration.

25. The method of claim 24, wherein a contoured insert is attached to the longitudinal edge of the portions extending laterally outward beyond the liner sheets, and the elongated guide rails have a groove with a contoured configuration complementary to the insert, and wherein inserting the contoured pack toward the rear face of the device further comprises slidably receiving the contoured insert in the contoured grooves of the elongated guide rails to securely retain the inserts within the grooves to hold the liner pack substantially flush against the bore wall surface in its generally curved configuration.

\* \* \* \* \*